US006613091B1

(12) United States Patent
Zdeblick et al.

(10) Patent No.: US 6,613,091 B1
(45) Date of Patent: Sep. 2, 2003

(54) SPINAL FUSION IMPLANTS AND TOOLS FOR INSERTION AND REVISION

(75) Inventors: Thomas Zdeblick, Middleton, WI (US); William F. McKay, Memphis, TN (US); Larry Boyd, Memphis, TN (US); Eddie Ray, III, Cordova, TN (US); Thomas McGahan, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/502,731

(22) Filed: Feb. 11, 2000

Related U.S. Application Data

(63) Continuation of application No. 08/803,541, filed on Feb. 20, 1997, now abandoned, which is a continuation of application No. 08/799,114, filed on Feb. 11, 1997, now abandoned, which is a continuation-in-part of application No. 08/603,674, filed on Feb. 19, 1996, now Pat. No. 5,984,967, which is a continuation-in-part of application No. 08/413,353, filed on Mar. 30, 1995, now Pat. No. 5,669,909, which is a continuation-in-part of application No. 08/411,017, filed on Mar. 27, 1995, now Pat. No. 5,782,919.

(51) Int. Cl.$^7$ .................................................. A61F 2/44
(52) U.S. Cl. .................................. 623/17.16; 623/17.11
(58) Field of Search ............................. 606/60, 61, 62, 606/70, 71, 72, 73; 623/17.11, 17.12, 17.16, 22.46

(56) References Cited

U.S. PATENT DOCUMENTS

| 3,486,505 A | 12/1969 | Morrison ..................... 128/303 |
| 3,848,601 A | 11/1974 | Ma et al. ..................... 128/305 |
| 4,309,777 A | 1/1982 | Patil ............................. 3/1.91 |

(List continued on next page.)

FOREIGN PATENT DOCUMENTS

| CA | 2015507 | 4/1990 |
| DE | 3505567 A | 6/1986 |
| EP | 077159 | 10/1982 |

(List continued on next page.)

OTHER PUBLICATIONS

*Replacement of the Lumbar of Sheep with Ceramic Prostheses*, Yamamuro, Shikata, Okumura, Kitsugi, Kakutani, Matsui, Kokubo, The Journal of Bone and Joint Surgery; vol. 72–B, No. 5, Sep. 1990.

(List continued on next page.)

*Primary Examiner*—Paul B. Prebilic
(74) *Attorney, Agent, or Firm*—Woodard, Emhardt, Moriarty, McNett & Henry LLP

(57) ABSTRACT

An interbody fusion device in one embodiment includes a tapered body defining a hollow interior or chamber for receiving bone graft or bone substitute material. The body defines exterior threads which are interrupted over portions of the outer surface of the device. The fusion device includes truncated side walls so that on end view the body takes on a cylindrical form. In another embodiment, the tapered body is solid and formed of a porous biocompatible material having sufficient structural integrity to maintain the intradiscal space and normal curvature. The material is preferably a porous tantalum composite having fully interconnected pores to facilitate complete bone tissue ingrowth into the implant. In further embodiments, the fusion devices are provided with osteogenic material to facilitate bone ingrowth. A cap is also provided to block the opening of hollow fusion devices. The cap includes an occlusion body and an elongated anchor. In some embodiments the anchor includes a lip which is engageable to openings in the body wall.

26 Claims, 18 Drawing Sheets

U.S. PATENT DOCUMENTS

| | | | |
|---|---|---|---|
| 4,349,921 A | 9/1982 | Kuntz | 3/1 |
| 4,501,269 A | 2/1985 | Bagby | 128/92 |
| 4,526,909 A | 7/1985 | Urist | 523/115 |
| 4,545,374 A | 10/1985 | Jacobson | 128/303 |
| 4,573,448 A | 3/1986 | Kambin | 128/1 |
| 4,596,574 A | 6/1986 | Urist | 623/16 |
| 4,599,086 A | 7/1986 | Doty | 623/27 |
| 4,627,853 A | 12/1986 | Campbell et al. | 623/16 |
| 4,714,469 A | 12/1987 | Kenna | 623/17 |
| 4,736,738 A | 4/1988 | Lipovsek et al. | 128/92 |
| 4,743,256 A | 5/1988 | Brantigan | 623/17 |
| 4,759,766 A | 7/1988 | Buettner-Janz et al. | 623/17 |
| 4,772,287 A | 9/1988 | Ray et al. | 623/17 |
| 4,820,305 A | 4/1989 | Harms et al. | 623/16 |
| 4,834,757 A | 5/1989 | Brantigan | 623/17 |
| 4,863,476 A | 9/1989 | Shepperd | 623/17 |
| 4,877,020 A | 10/1989 | Vich | 128/92 |
| 4,878,915 A | 11/1989 | Brantigan | 623/17 |
| 4,892,545 A | 1/1990 | Day et al. | 623/17 |
| 4,904,261 A | 2/1990 | Dove et al. | 623/17 |
| 4,917,704 A | 4/1990 | Frey et al. | 623/17 |
| 4,932,975 A | 6/1990 | Main et al. | 623/17 |
| 4,936,848 A | 6/1990 | Bagby | 623/17 |
| 4,961,740 A | 10/1990 | Ray et al. | 606/61 |
| 5,002,576 A | 3/1991 | Fuhrmann et al. | 623/17 |
| 5,015,247 A | 5/1991 | Michelson | 606/61 |
| 5,030,474 A | 7/1991 | Saita et al. | 427/2 |
| 5,055,104 A | 10/1991 | Ray | 606/61 |
| 5,062,850 A | 11/1991 | MacMillan et al. | 623/17 |
| 5,068,122 A | 11/1991 | Kokubo et al. | 427/2 |
| 5,071,437 A | 12/1991 | Steffee | 623/17 |
| 5,128,169 A | 7/1992 | Saita et al. | 427/2 |
| 5,133,755 A | 7/1992 | Brekke | 623/16 |
| RE34,037 E | 8/1992 | Inoue et al. | 604/93 |
| 5,147,402 A | 9/1992 | Bohler et al. | 623/16 |
| 5,147,404 A | 9/1992 | Downey | 623/17 |
| 5,164,187 A | 11/1992 | Constantz et al. | 424/423 |
| 5,188,670 A | 2/1993 | Constantz | 118/667 |
| 5,192,327 A | 3/1993 | Brantigan | 623/17 |
| 5,207,710 A | 5/1993 | Chu et al. | 623/16 |
| 5,236,456 A | 8/1993 | O'Leary et al. | 623/16 |
| 5,236,460 A | 8/1993 | Barber | 623/17 |
| 5,258,029 A | 11/1993 | Chu et al. | 623/16 |
| 5,279,831 A | 1/1994 | Constantz et al. | 424/423 |
| 5,282,861 A | 2/1994 | Kaplan | 623/16 |
| 5,290,312 A | 3/1994 | Kojimoto et al. | 623/17 |
| 5,300,238 A | 4/1994 | Taylor et al. | 428/216 |
| 5,306,307 A | 4/1994 | Senter et al. | 623/17 |
| 5,306,309 A | 4/1994 | Wagner et al. | 623/17 |
| 5,306,310 A | 4/1994 | Siebels | 623/17 |
| 5,338,433 A | 8/1994 | Maybee et al. | 205/178 |
| 5,344,654 A | 9/1994 | Rueger et al. | 424/423 |
| 5,348,026 A | 9/1994 | Davidson | 128/898 |
| 5,360,430 A | 11/1994 | Lin | 606/61 |
| 5,366,508 A | 11/1994 | Brekke | 623/16 |
| 5,397,364 A | 3/1995 | Kozak et al. | 623/17 |
| 5,405,391 A | 4/1995 | Hednerson et al. | 623/17 |
| 5,423,816 A | 6/1995 | Lin | 606/61 |
| 5,423,817 A | 6/1995 | Lin | 623/17 |
| 5,425,772 A | 6/1995 | Brantigan | 623/16 |
| 5,439,464 A | 8/1995 | Shapiro | 606/83 |
| 5,443,514 A | 8/1995 | Steffee | 623/17 |
| 5,443,515 A | 8/1995 | Cohen et al. | 623/17 |
| 5,458,638 A | 10/1995 | Kuslich et al. | 623/17 |
| 5,484,437 A | 1/1996 | Michelson | 606/61 |
| 5,489,307 A | 2/1996 | Kuslich et al. | 623/17 |
| 5,489,308 A | 2/1996 | Kuslich et al. | 623/17 |
| 5,514,180 A | 5/1996 | Heggeness et al. | 623/17 |
| 5,554,191 A | 9/1996 | Lahille et al. | 623/17 |
| 5,562,736 A | 10/1996 | Ray et al. | 623/17 |
| D377,095 S | 12/1996 | Michelson | D24/155 |
| D377,096 S | 12/1996 | Michelson | D24/155 |
| 5,591,235 A | 1/1997 | Kuslich | 623/17 |
| 5,593,409 A | 1/1997 | Michelson | 606/61 |
| 5,601,556 A | 2/1997 | Pisharodi | 606/61 |
| 5,609,635 A | 3/1997 | Michelson | 623/17 |
| 5,609,636 A | 3/1997 | Kohrs et al. | 623/17 |
| 5,645,591 A | 7/1997 | Kuberasampath | 623/16 |
| 5,645,598 A | 7/1997 | Brosnahan, III | 623/17 |
| 5,658,285 A | 8/1997 | Marnay et al. | 606/61 |
| 5,669,909 A | 9/1997 | Zdeblick et al. | 606/61 |
| 5,683,394 A | 11/1997 | Rinner | 606/61 |
| 5,683,463 A | 11/1997 | Godefroy et al. | 623/17 |
| 5,702,451 A | 12/1997 | Biedermann et al. | 623/17 |
| 5,723,013 A | 3/1998 | Jeanson et al. | |
| 5,766,252 A | 6/1998 | Henry et al. | 623/17 |
| 5,766,253 A | 6/1998 | Brosnahan, III | 623/17 |
| D397,439 S | 8/1998 | Koros et al. | D24/155 |
| 5,888,228 A | 3/1999 | Knothe et al. | 623/17 |
| 5,931,840 A * | 8/1999 | Goble et al. | 606/73 |
| 5,980,522 A | 11/1999 | Koros et al. | 623/17 |
| 6,015,937 A * | 1/2000 | Branemark | 623/16 |
| 6,447,544 B1 * | 9/2002 | Michelson | 623/17.16 |
| 6,478,823 B1 * | 11/2002 | Michelson | 623/17.16 |

FOREIGN PATENT DOCUMENTS

| | | |
|---|---|---|
| EP | 0179695 | 9/1985 |
| EP | 0635246 | 1/1995 |
| EP | 646366 | 5/1995 |
| EP | 637440 | 8/1995 |
| FR | 2710519 A1 | 9/1993 |
| WO | WO 87/07827 | 12/1987 |
| WO | WO 90/00037 | 1/1990 |
| WO | WO 91/06261 | 5/1991 |
| WO | WO 92/14423 | 9/1992 |
| WO | WO 94/11040 | 5/1994 |
| WO | WO 94/26893 | 11/1994 |
| WO | WO 95/08306 | 3/1995 |
| WO | WO 95/15133 | 6/1995 |
| WO | WO96/22747 | 8/1996 |

OTHER PUBLICATIONS

*Healing Segmental Femoral Defects in Sheep Using Recombinant Human Bone Morphogenetic Protein*, Gerhart, Kirker–Head, Kriz, Holtrop, Hennig, Hipp, Schelling, Wang, Clincial Orthopaedics and Related Research, No. 293, pp. 317–326, 1993.

*The Treatment of Certain Cervical–Spine Disorders by Anterior Removal of the Intervertebral Disc and Interbody Fusion*, Smith, Robinson; The Journal of Bone and Joint Surgery; vol. 49–a, No. 3, Jun. 1958.

* cited by examiner

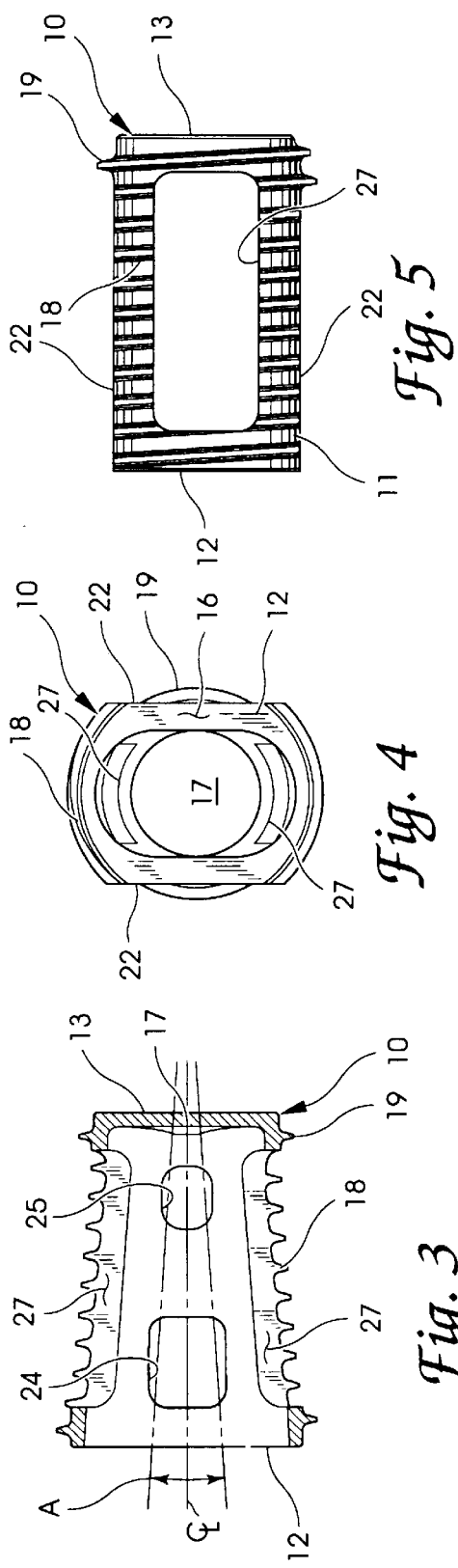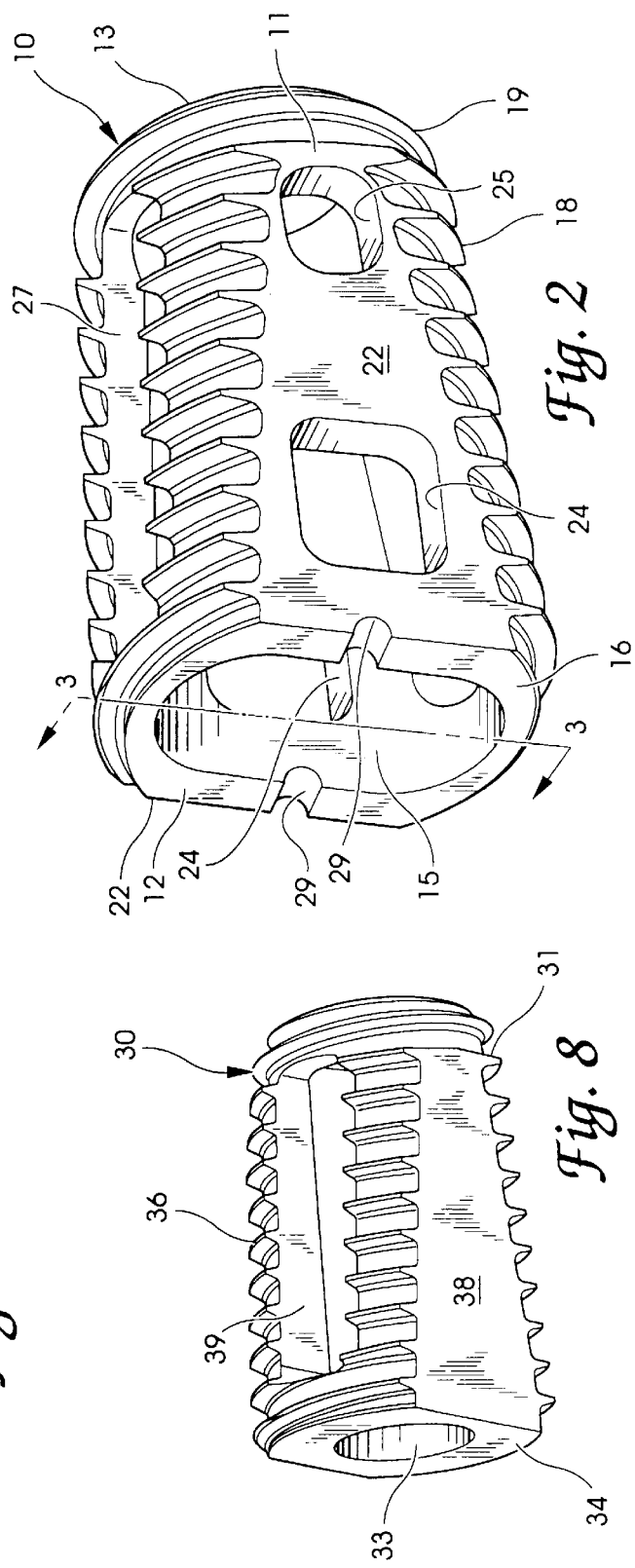

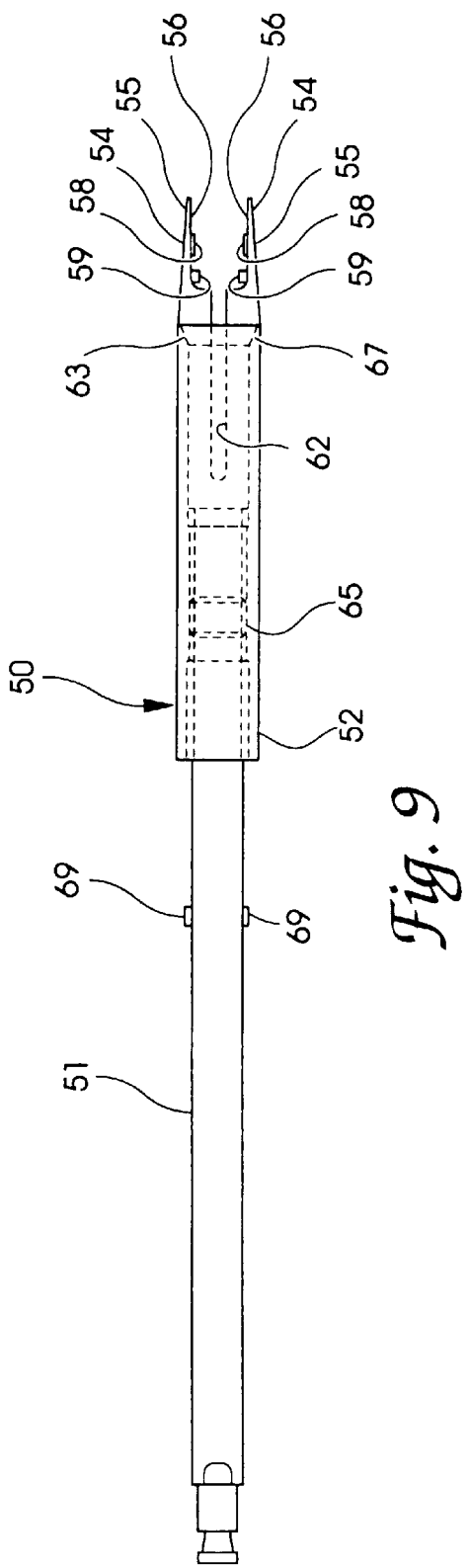
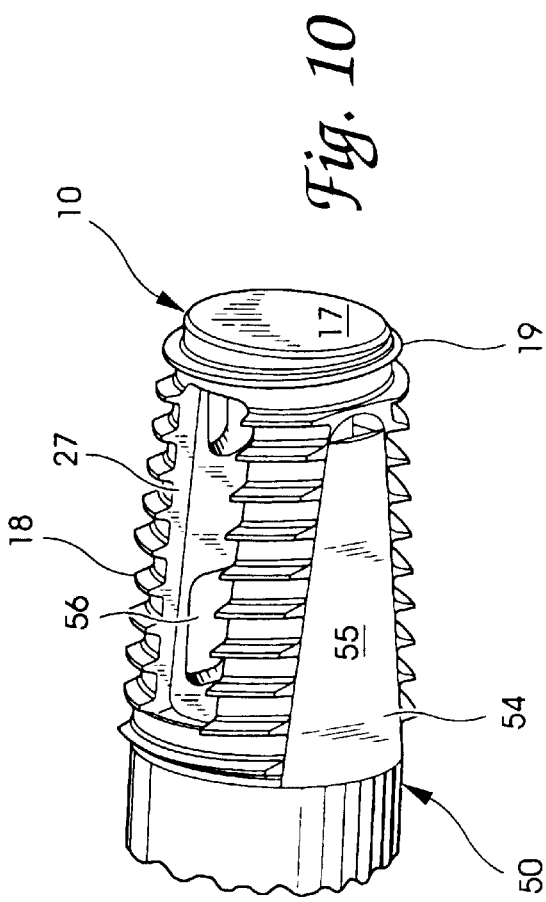
Fig. 9
Fig. 10

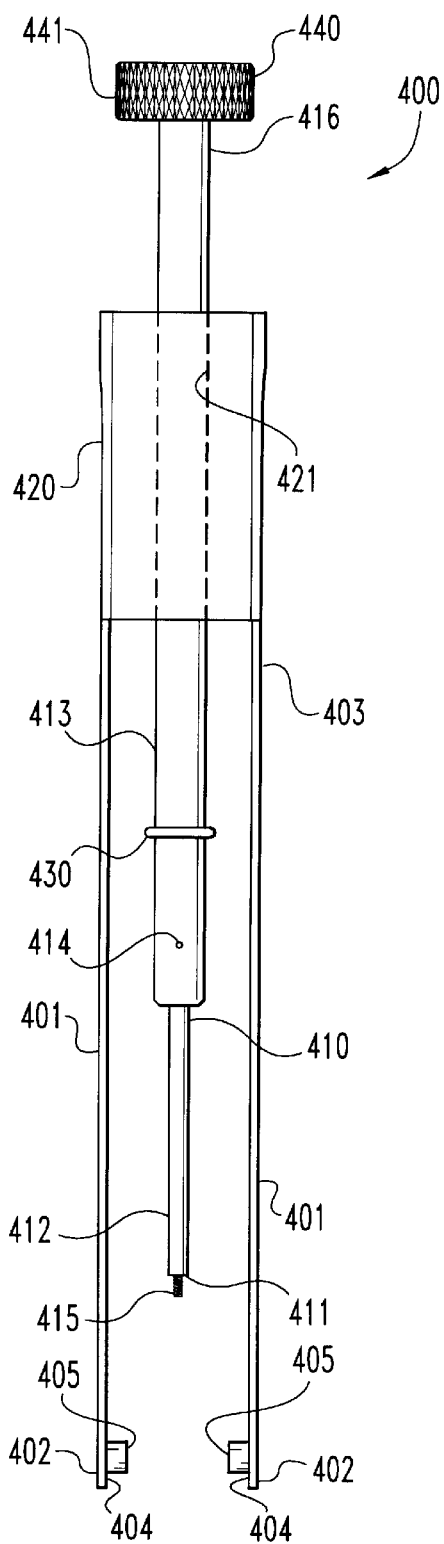
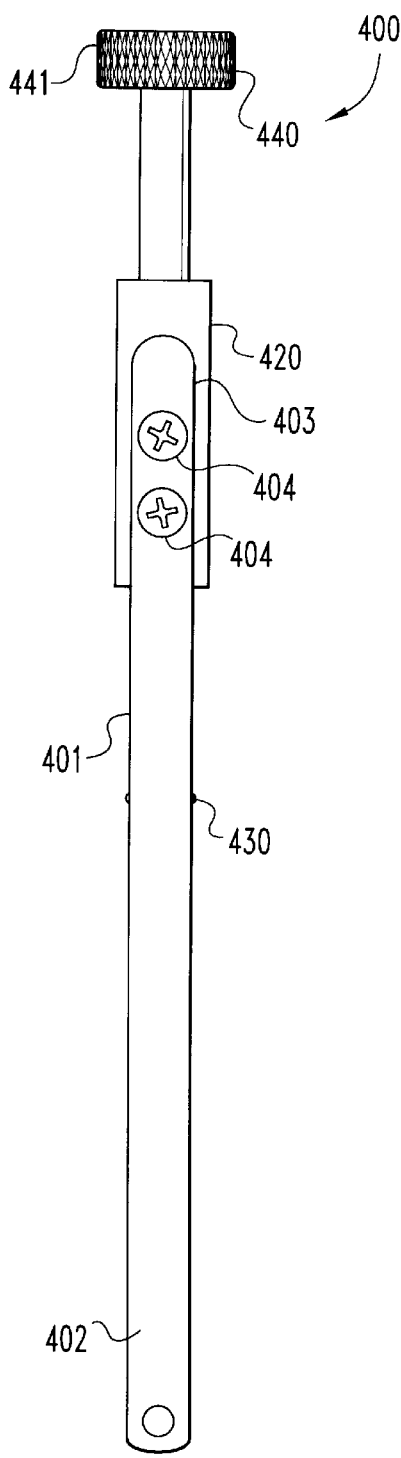
Fig. 19                     Fig. 20

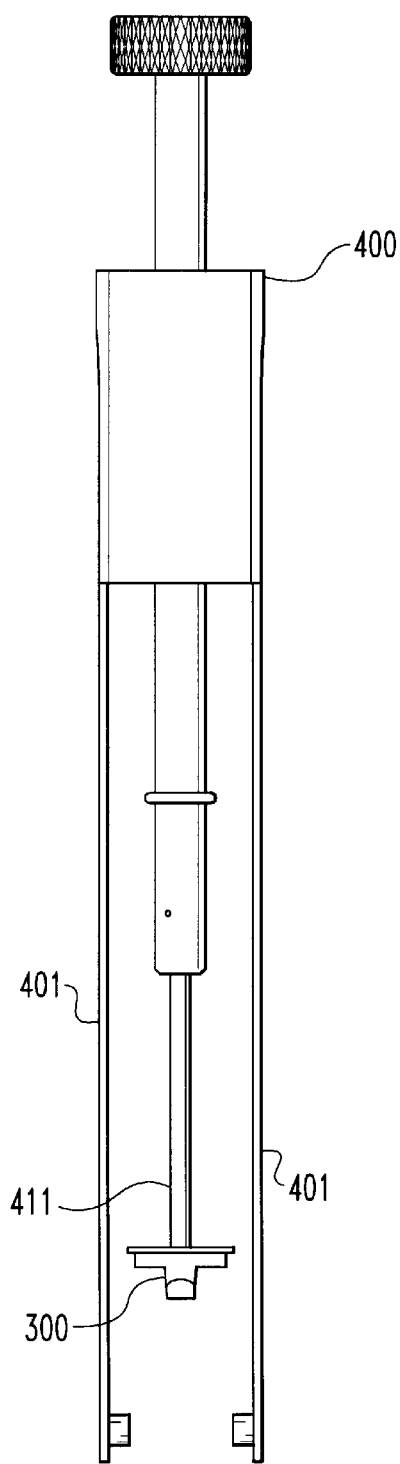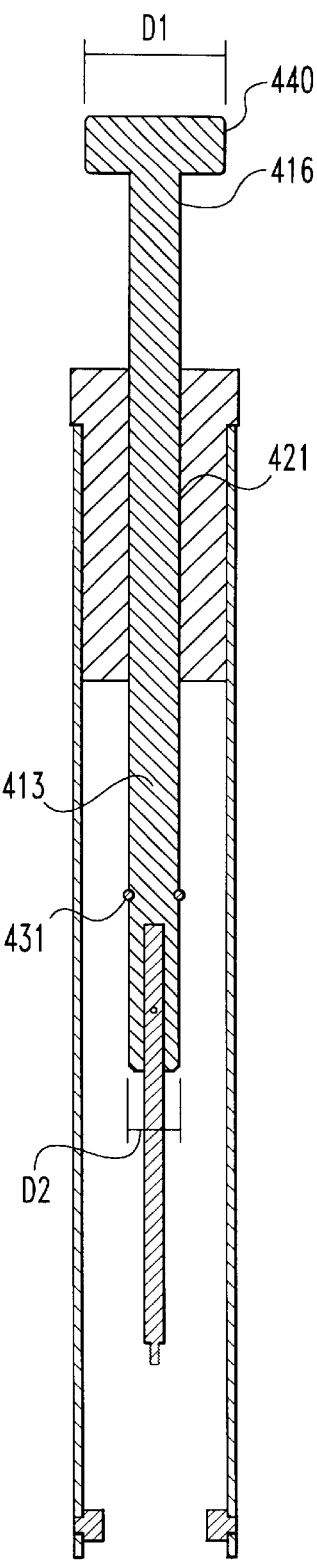
Fig. 22                    Fig. 25

SPINAL FUSION IMPLANTS AND TOOLS FOR INSERTION AND REVISION

The present application is a continuation of U.S. patent application Ser. No. 08/803,541 filed on Feb. 20, 1997, now abandoned; which is a continuation of U.S. patent application Ser. No. 08/799,114 filed on Feb. 11, 1997, now abandoned; which is a continuation-in-part of U.S. patent application Ser. No. 08/603,674 filed on Feb. 19, 1996, now issued as U.S. Pat. No. 5,984,967; which is a continuation-in-part of U.S. patent application Ser. No. 08/413,353 filed on Mar. 30, 1995, now issued as U.S. Pat. No. 5,669,909; which is a continuation-in-part of U.S. patent application Ser. No. 08/411,017 filed on Mar. 27, 1995, now issued as U.S. Pat. No. 5,782,919.

BACKGROUND OF THE INVENTION

The present invention relates to an artificial implant to be placed into the intervertebral space left after the removal of a damaged spinal disc. Specifically, the invention concerns an implant that facilitates arthrodesis or fusion between adjacent vertebrae while also maintaining or restoring the normal spinal anatomy at the particular vertebral level.

The number of spinal surgeries to correct the causes of low back pain has steadily increased over the last several years. Most often, low back pain originates from damage or defects in the spinal disc between adjacent vertebrae. The disc can be herniated or can be suffering from a variety of degenerative conditions, so that in either case the anatomical function of the spinal disc is disrupted. The most prevalent surgical treatment for these types of conditions has been to fuse the two vertebrae surrounding the affected disc. In most cases, the entire disc will be removed, except for the annulus, by way of a discectomy procedure. Since the damaged disc material has been removed, something must be positioned within the intradiscal space, otherwise the space may collapse resulting in damage to the nerves extending along the spinal column.

In order to prevent this disc space collapse and to stabilize the spine, the intradiscal space is filled with bone or a bone substitute in order to fuse the two adjacent vertebrae together. In early techniques, bone material was simply disposed between the adjacent vertebrae, typically at the posterior aspect of the vertebrae, and the spinal column was stabilized by way of a plate or a rod spanning the affected vertebrae. With this technique once fusion occurred the hardware used to maintain the stability of the segment became superfluous. Moreover, the surgical procedures necessary to implant a rod or plate to stabilize the level during fusion were frequently lengthy and involved.

It was therefore determined that a more optimum solution to the stabilization of an excised disc space is to fuse the vertebrae between their respective end plates, most optimally without the need for anterior or posterior plating. There have been an extensive number of attempts to develop an acceptable intradiscal implant that could be used to replace a damaged disc and yet maintain the stability of the disc interspace between the adjacent vertebrae, at least until complete arthrodesis is achieved. These "interbody fusion devices" have taken many forms. For example, one of the more prevalent designs takes the form of a cylindrical implant. These types of implants are represented by the patents to Bagby, U.S. Pat. No. 4,501,269; Brantigan, U.S. Pat. No. 4,878,915; Ray, U.S. Pat. Nos. 4,961,740 and 5,055,104; and Michelson, U.S. Pat. No. 5,015,247. In these cylindrical implants, the exterior portion of the cylinder can be threaded to facilitate insertion of the interbody fusion device, as represented by the Ray, Brantigan and Michelson patents. In the alternative, some of the fusion implants are designed to be pounded into the intradiscal space and the vertebral end plates. These types of devices are represented by the patents to Brantigan, U.S. Pat. Nos. 4,743,256; 4,834,757 and 5,192,327.

In each of the above listed patents, the transverse cross section of the implant is constant throughout its length and is typically in the form of a right circular cylinder. Other implants have been developed for interbody fusion that do not have a constant cross section. For instance, the patent to McKenna, U.S. Pat. No. 4,714,469 shows a hemispherical implant with elongated protuberances that project into the vertebral end plate. The patent to Kuntz, U.S. Pat. No. 4,714,469, shows a bullet shaped prosthesis configured to optimize a friction fit between the prosthesis and the adjacent vertebral bodies. Finally, the implant of Bagby, U.S. Pat. No. 4,936,848 is in the form of a sphere which is preferably positioned between the centrums of the adjacent vertebrae.

Interbody fusion devices can be generally divided into two basic categories, namely solid implants and implants that are designed to permit bone ingrowth. Solid implants are represented by U.S. Pat. Nos. 4,878,915; 4,743,256; 4,349,921 and 4,714,469. The remaining patents discussed above include some aspect that permits bone to grow across the implant. It has been found that devices that promote natural bone ingrowth achieve a more rapid and stable arthrodesis. The device depicted in the Michelson patent is representative of this type of hollow implant which is typically filled with autologous bone prior to insertion into the intradiscal space. This implant includes a plurality of circular apertures which communicate with the hollow interior of the implant, thereby providing a path for tissue growth between the vertebral end plates and the bone or bone substitute within the implant. In preparing the intradiscal space, the adjacent end plates are preferably reduced to bleeding bone to facilitate this tissue ingrowth. During fusion, the metal structure provided by the Michelson implant helps maintain the patency and stability of the motion segment to be fused. In addition, once arthrodesis occurs, the implant itself serves as a sort of anchor or scaffold for the solid bony mass.

A number of difficulties still remain with the many interbody fusion devices currently available. While it is recognized that hollow implants that permit bone ingrowth into bone or bone substitute within the implant are an optimum technique for achieving fusion, most of the prior art devices have difficulty in achieving this fusion, at least without the aid of some additional stabilizing device, such as a rod or plate. Moreover, some of these devices are not structurally strong enough to support the heavy loads and bending moments applied at the most frequently fused vertebral levels, namely those in the lower lumbar spine.

There has been a need for providing a hollow interbody fusion device that optimizes the bone ingrowth capabilities but is still strong enough to support the spine segment until arthrodesis occurs. It has been found by the present inventors that openings for bone ingrowth play an important role in avoiding stress shielding of the autologous bone impacted within the implant. In other words, if the ingrowth openings are improperly sized or configured, the autologous bone will not endure the loading that is typically found to be necessary to ensure rapid and complete fusion. In this instance, the bone impacted within the implant may resorb or evolve into simply fibrous tissue, rather than a bony fusion mass, which leads to a generally unstable construction. On the other hand, the bone ingrowth openings must not be so extensive that the cage provides insufficient support area to avoid subsidence into the adjacent vertebrae.

The use of bone graft materials in past metal cage fusion devices has presented several disadvantages. Autograft is undesirable because existing structures may not yield a sufficient quantity of graft material. The additional surgery to extract the autograft also increases the risk of infection and may reduce structural integrity at the donor site. Furthermore, many patients complain of significant pain for several years after the donor surgery. Although, the supply of allograft material is not so limited, allograft is also disadvantageous because of the risk of disease transmission and immune reactions. Furthermore, allogenic bone does not have the osteogenic potential of autogenous bone and therefore will incorporate more slowly and less extensively.

These disadvantages have led to the investigation of bioactive substances that regulate the complex cascade of cellular events of bone repair. Such substances include bone morphogenetic proteins, for use as alternative or adjunctive graft materials. Bone morphogenetic proteins (BMPs), a class of osteoinductive factors from bone matrix, are capable of inducing bone formation when implanted in a fracture or surgical bone site. Recombinantly produced human bone morphogenetic protein-2 (rhBMP-2) has been demonstrated in several animal models to be effective in regenerating bone in skeletal defects. The use of such proteins has led to a need for appropriate carriers and fusion device designs.

SUMMARY OF THE INVENTION

In response to the needs still left unresolved by the prior devices, the present invention contemplates a hollow threaded interbody fusion device configured to restore the normal angular relation between adjacent vertebrae. In particular, the device includes an elongated body, tapered along substantially its entire length, defining a hollow interior and having an outer diameter greater than the size of the space between the adjacent vertebrae. The body includes an outer surface with opposite tapered cylindrical portions and a pair of opposite flat tapered side surfaces between the cylindrical portions. Thus, at an end view, the fusion device gives the appearance of a cylindrical body in which the sides of the body have been truncated along a chord of the body's outer diameter. The cylindrical portions are threaded for controlled insertion and engagement into the end plates of the adjacent vertebrae.

In another aspect of the invention, the outer surface is tapered along its length at an angle corresponding, in one embodiment, to the normal lordotic curvature of lower lumbar vertebrae. The outer surface is also provided with a number of vascularization openings defined in the flat side surfaces, and a pair of elongated opposite bone ingrowth slots defined in the cylindrical portions. The bone ingrowth slots have a transverse width that is preferably about half of the effective width of the cylindrical portions within which the slots are defined.

In another embodiment, the interbody fusion device retains the same tapered configuration of the above embodiment, along with the truncated side walls and interrupted external threads. However, in this embodiment, the implant is not hollow but is instead solid. Bone ingrowth is achieved by forming the solid tapered implant of a porous high strength material that permits bone ingrowth into interconnected pores while retaining sufficient material for structural stability in situ. In one preferred embodiment, the material is a porous tantalum composite.

In another aspect of this invention, a hollow interbody fusion device is provided with an osteogenic material to optimize fusion. The osteogenic material comprises an osteoinductive protein in a suitable carrier.

In still another embodiment, the interbody fusion device is solid instead of hollow and is composed of a porous high strength material that permits bone ingrowth into interconnected pores. In one preferred embodiment, the material is coated with an osteoinductive material.

In another aspect a cap is provided which securely blocks the opening in a fusion device to prevent expulsion of an osteogenic material from within the device. The cap includes an occlusion body for blocking the opening and an elongated anchor for securing the occlusion body within the opening. In some embodiments the anchor includes a lip which is engageable to openings in the body wall.

In still another embodiment a tool is provided for manipulating caps for interbody fusion devices. In one embodiment the tool includes a pair of prongs each having facing engagement surfaces for engaging the fusion device, and a shaft slidably disposed between the prongs. The shaft has a cap-engaging tip for engaging a tool hole in the cap. The prongs include a pair of releasing members on each of the facing engagement surfaces. The releasing members have a height and a width for being insertable into apertures in a body wall in the fusion device to disengage elongate anchors of the cap from the apertures.

DESCRIPTION OF THE FIGURES

FIG. 2 is an enlarged perspective view of an interbody fusion device according to one embodiment of the present invention.

FIG. 3 is a side cross-sectional view of the interbody fusion device shown in FIG. 2, taken along line 3—3 as viewed in the direction of the arrows.

FIG. 4 is an end elevational view from the anterior end of the interbody fusion device shown in FIG. 2.

FIG. 5 is a top-elevational view of the interbody fusion device shown in FIG. 2.

FIG. 8 is a perspective view of an alternative embodiment of the interbody fusion device according to the present invention.

FIG. 9 is a top-elevational view of an implant driver according to another aspect of the present invention.

FIG. 10 is an enlarged perspective view of the end of the implant driver engaged about an interbody fusion device, as depicted in FIG. 2.

FIG. 19 is an elevational view of a cap manipulating tool of this invention.

FIG. 20 is a side elevational view of the tool depicted in FIG. 19.

FIG. 22 is an elevational view of the tool of FIG. 19 engaged to a cap.

FIG. 25 is a partial cross-sectional view of the tool of FIG. 19.

DESCRIPTION OF THE PREFERRED EMBODIMENTS

Figure 1:
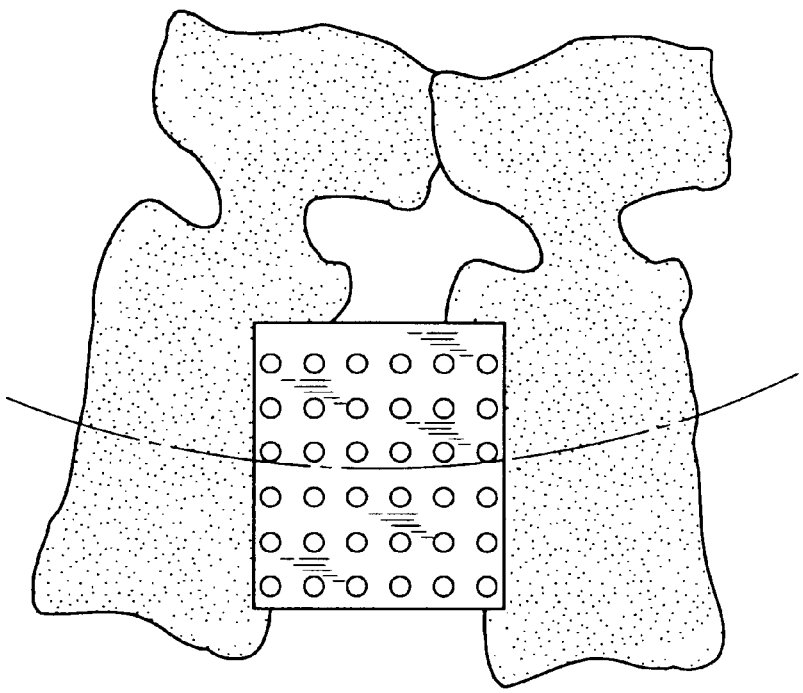
FIG. 1 is a side-elevational view in the sagittal plane of a fusion device of the prior art.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

An interbody fusion device 10 in accordance with one aspect of the present invention is shown in FIGS. 2–5. The device is formed by a solid, conical, load bearing body 11, that is preferably formed of a biocompatible or inert material. For example, the body 11 can be made of a medical grade stainless steel or titanium, or other suitable material having adequate strength characteristics set forth herein. The device may also be composed of a biocompatible porous material, such as a porous tantalum composite provided by Implex Corp. For purposes of reference, the device 10 has an anterior end 12 and a posterior end 13, which correspond to the anatomic position of the device 10 when implanted in the intradiscal space. The conical body 11 defines a chamber or hollow interior 15 which is bounded by a body wall 16 and closed at the posterior end 13 by an end wall 17 (see FIG. 3). The hollow interior 15 of the device 10 is configured to receive autograft bone or a bone substitute material adapted to promote a solid fusion between adjacent vertebrae and across the intradiscal space.

In accordance with the invention, the interbody fusion device 10 is a threaded device configured to be screw threaded into the end plates of the adjacent vertebrae. In one embodiment of the invention, the conical body 11 defines a series of interrupted external threads 18 and a complete thread 19 at the leading end of the implant. The complete thread 19 serves as a "starter" thread for screwing the implant into the vertebral endplates at the intradiscal space. The threads 18 and 19 can take several forms known in the art for engagement into vertebral bone. For instance, the threads can have a triangular cross-section or a truncated triangular cross-section. Preferably, the threads have a height of 1.0 mm (0.039 in) in order to provide adequate purchase in the vertebral bone so that the fusion device 10 is not driven out of the intradiscal space by the high loads experienced by the spine. The thread pitch in certain specific embodiments can be 2.3 mm (0.091 in) or 3.0 mm (0.118 in), depending upon the vertebral level at which the device 10 is to be implanted and the amount of thread engagement necessary to hold the implant in position.

In one aspect of the invention, the conical body 11, and particularly the body wall 16, includes parallel truncated side walls 22, shown most clearly in FIG. 4. The side walls are preferably flat to facilitate insertion of the fusion device between the end plates of adjacent vertebrae and provide area between for bony fusion. The truncated side walls extend from the anterior end 12 of the device up to the complete threads 19 at the posterior end 13. Thus, with the truncated side walls 22, the device 10 gives the appearance at its end view of an incomplete circle in which the sides are cut across a chord of the circle. In one specific example, the interbody fusion device 10 has a diameter at its anterior end of 16.0 mm (0.630 in). In this specific embodiment, the truncated side walls 22 are formed along parallel chord lines approximately 12.0 mm (0.472 in) apart, so that the removed arc portion of the circle roughly subtends 90° at each side of the device. Other benefits and advantages provided by the truncated side walls 22 of the fusion device 10 will be described in more detail herein.

To promote fusion, the devices of this invention may be provided with apertures defined through the body wall 16. The device 10 depicted in FIGS. 2–5 includes two types of body wall apertures, vascularization openings 24, 25 and bone ingrowth slots 27 as described below.

The conical body 11 of the device 10 includes a pair of vascularization openings 24 and 25 defined through each of the truncated side walls 22. These openings 24 and 25 are adapted to be oriented in a lateral direction or facing the sagittal plane when the fusion device is implanted within the intradiscal space. The openings are intended to provide a passageway for vascularization to occur between the bone implant material within the hollow interior 15 and the surrounding tissue. In addition, some bone ingrowth may also occur through these openings. The openings 24 and 25 have been sized to provide optimum passage for vascularization to occur, while still retaining a significant amount of structure in the conical body 11 to support the high axial loads passing across the intradiscal space between adjacent vertebrae.

The conical body 11 also defines opposite bone ingrowth slots 27, each of which are oriented at 90° to the truncated side walls 22. Preferably, these slots 27 are directly adjacent the vertebral end plates when the device 10 is implanted. More particularly, as the threads 18 and 19 of the device are screwed into the vertebral endplates, the vertebral bone will extend partially into the slots 27 to contact bone implant material contained within the hollow interior 15 of the device 10. As shown more clearly in FIG. 5, the bone ingrowth slots 27 are configured to provide maximum opening for bone ingrowth, in order to ensure complete arthrodesis and a solid fusion. Preferably, the slots have a lateral width that approximates the effective width of the threaded portions of the body.

Smaller apertures can lead to pseudo-arthrosis and the generation of fibrous tissue. Since the bone ingrowth slots 27 of the present invention are directly facing the vertebrae, they are not situated in a portion of the device that must bear high loads. Instead, the truncated side walls 22 will bear most of the load passing between the vertebral end plates through the interrupted threads 18 and across the intradiscal space.

In a further feature, the anterior end 12 of the body wall 16 can define a pair of diametrically opposed notches 29, which are configured to engage an implant driver tool as described herein. Moreover, the end wall 17 at the posterior end 13 of the implant can be provided with a tool engagement feature (not shown). For example, a hex recess can be provided to accommodate a hex driver tool, as described further herein.

In one important feature of the interbody fusion device of the present invention, the body 11 includes a tapered or conical form. In other words, the outer diameter of the device at its anterior end 12 is larger than the outer diameter at the posterior end 13. As depicted in FIG. 3, the body wall 16 tapers at an angle A about the centerline CL of the device 10. The taper of the body wall 16 is adapted to restore the normal relative angle between adjacent vertebrae. For example, in the lumbar region, the angle A is adapted to restore the normal lordotic angle and curvature of the spine in that region. In one specific example, the angle A is 8.794°. It is understood that the implant may have non-tapered portions, provided that the portions do not otherwise interfere with the function of the tapered body.

Figure 7:
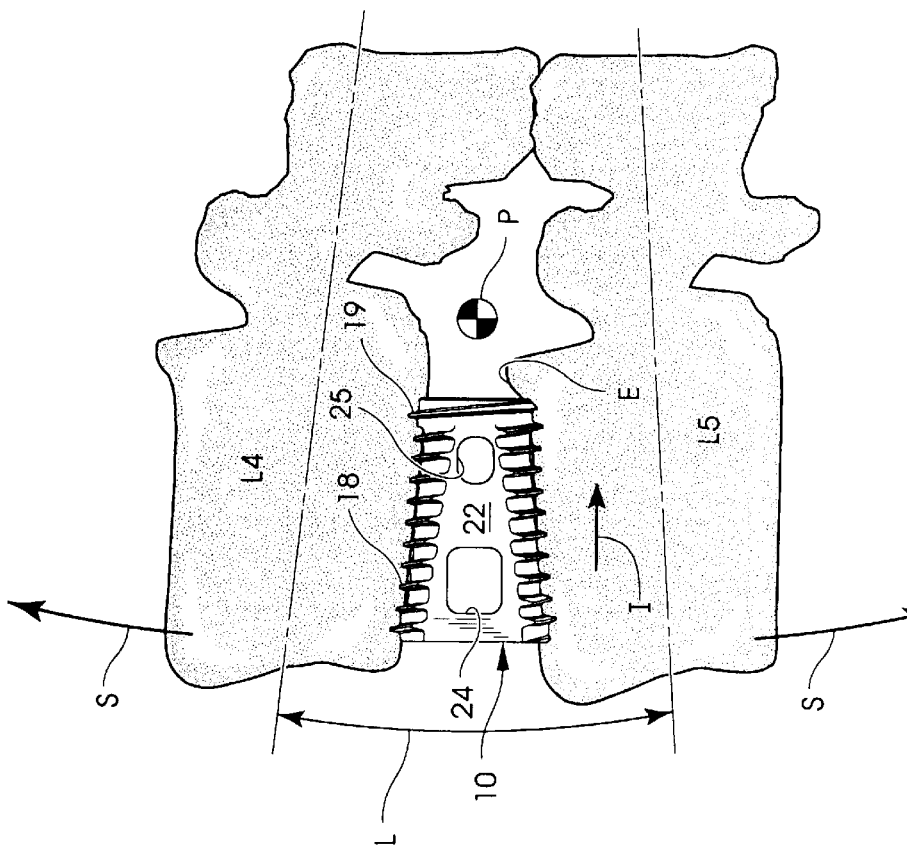
FIG. 7 is a sagittal plane view of the interbody fusion device implanted between L4 and L5 shown in FIG. 6.

The taper angle A of the implant, coupled with the outer diameter at the anterior and posterior ends of the fusion device 10, define the amount of angular spreading that will occur between the adjacent vertebrae as the implant is placed or screwed into position. This feature is depicted more clearly in FIGS. 6 and 7 in which a preferred construct employing a pair of fusion devices 10 is shown. In the depicted construct, the devices 10 are disposed between the lower lumbar vertebrae L4 and L5, with the threads 18 and 19 threaded into the end plates E of the two vertebrae. As shown in FIG. 7, as the device 10 is threaded into the end plates E, it advances in the direction of the arrow I toward the pivot axis P of the vertebral level. The pivot axis P is nominally the center of relative rotation between the adjacent vertebrae of the motion segment. As the tapered fusion device 10 is driven further in the direction of the arrow I toward the pivot axis P, the adjacent vertebrae L4 and L5 are angularly spread in the direction of the arrows S. Depth of insertion of the fusion device 10 will determine the ultimate lordotic angle L achieved between the two vertebrae.

In specific embodiments of the implant 10, the outer diameter or thread crest diameter at the anterior end 12 can be 16, 18 or 20 mm, and the overall length of the device 26 mm. The sizing of the device is driven by the vertebral level into which the device is implanted and the amount of angle that must be developed.

Figure 6:
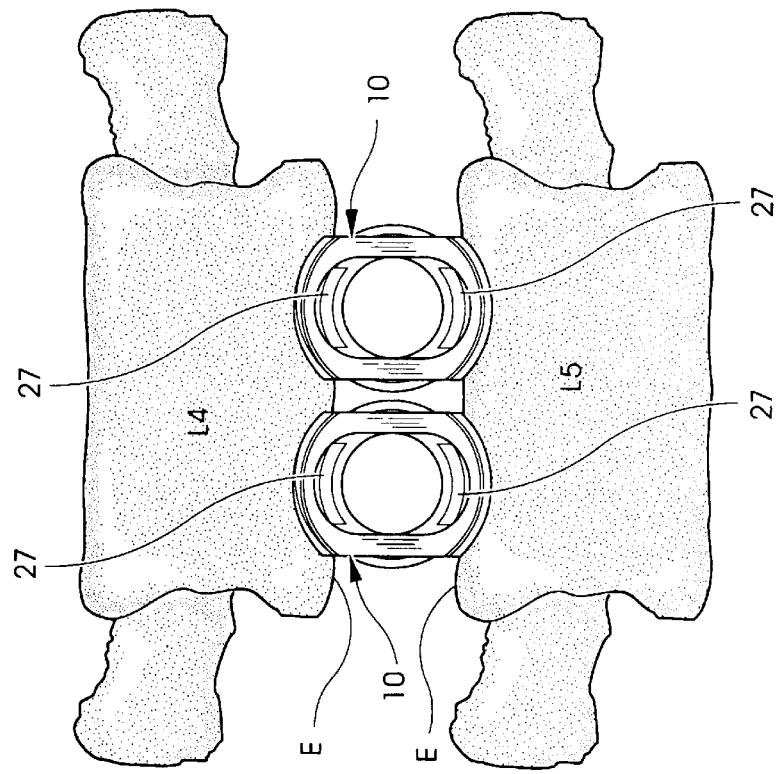
FIG. 6 is an A-P lateral view from the anterior aspect of the spine showing two interbody fusion devices according to FIG. 2 implanted within the interbody space between L4 and L5.

In another aspect of the invention, device 10 is sized so that two such cylindrical bodies 11 can be implanted into a single disc space, as shown in FIG. 6. This permits the placement of additional bone graft material between and around the devices 10 in situ. This aspect further promotes fusion across the intradiscal space and also serves to more firmly anchor the devices between the adjacent vertebrae to prevent expulsion due to the high axial loads at the particular vertebral level.

In one specific embodiment of the interbody fusion device 10, the vascularization opening 24 is generally rectangular in shape having dimensions of 6.0 mm (0.236 in) by 7.0 mm (0.276 in). Similarly, the vascularization opening 25 is rectangular with dimensions of 4.0 mm (0.157 in) by 5.0 mm (0197 in). Naturally, this opening is smaller because it is disposed at the smaller posterior end 13 of the device 10. The bone ingrowth slots 27 are also rectangular in shape with a long dimension of 20.0 mm (0.787 in) and a width of 6.0 mm (0.236 in). It has been found that these dimensions of the vascularization openings 24, 25 and slots 27 provide optimum bone ingrowth and vascularization. In addition, these openings are not so large that they compromise the structural integrity of the device or that they permit the bone graft material contained within the hollow interior 15 to be easily expelled during implantation.

As can be seen in FIG. 7, when the device is in position between the L4 and L5 vertebrae, the vascularization openings 24 and 25 are side facing to contact the highly vascularized tissue surrounding the vertebrae. In addition, as can be seen in FIG. 6, the bone ingrowth slots 27 are axially directed so that they contact the vertebral end plates E.

In an alternative embodiment of the invention, shown in FIG. 8, an interbody fusion device 30 is formed of a conical, load bearing body 31. The body wall 34 defines a chamber or hollow interior 33 as with the fusion device 10 of the previous embodiment. However, in this embodiment the truncated side wall 38 does not include any vascularization openings. Moreover, the bone ingrowth slots 39 on opposite sides of the device 30 are smaller. This means that the interrupted threads 36 on the exterior of the device 30 extend a greater length around the implant. Such a design could be utilized if a porous material (e.g., a porous tantalum composite) were used to provide additional surface area for tissue ingrowth and anchorage to the adjacent bone or if a bone growth promoting protein were used to increase the fusion rate. Also, this interbody fusion device 30 of the embodiment shown in FIG. 8 can have application at certain vertebral levels where the risk of expulsion of the device is greatest. Consequently, the amount of thread contact is increased to prevent such expulsion. Prior to insertion, the hollow interior 15 of the fusion device 10 is filled completely with bone or substitute to facilitate this pre-loading.

Figure 8A:
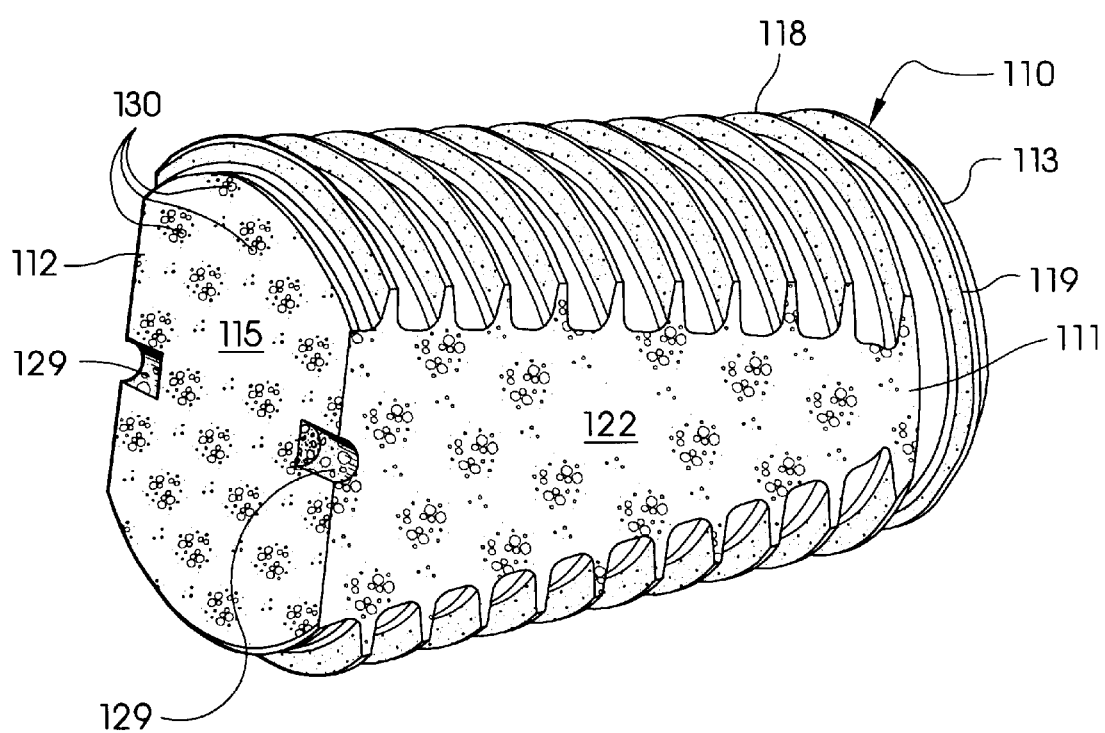
FIG. 8A is a perspective view of another embodiment of a tapered interbody fusion device according to the present invention.

In a further embodiment using a porous material, the interbody fusion device 110 of FIG. 8A retains the tapered configuration of the previous embodiments, but is solid instead of hollow. The device 110 comprises a tapered, load bearing body 111 having a larger outer diameter at is anterior end 112 than at is posterior end 113. The entire body 111 is solid leaving a closed surface, such as surface 115, at both ends of the implant. The device includes the interrupted threads 118, starter threads 119 and truncated side walls 122 of the prior embodiments. A driving tool slot 129 can also be defined in the end surface 115. Alternatively, the starter threads 119 can be eliminated leaving an unthreaded cylindrical portion at the posterior end of the implant. Similarly, the driving tool slot 129 take on many configurations depending upon the design of the tool used to insert the device 110 into the intradiscal space.

The benefits of the embodiment of the fusion device shown in FIG. 8A are especially appreciated by the use of a porous, high strength material to form the solid body 111. In the preferred embodiment, this material is a porous tantalum-carbon composite marketed by Implex Corp. under the tradename HEDROCEL® and described in U.S. Pat. No. 5,282,861 to Kaplan, which description is incorporated herein by reference. Due to the nature of the HEDROCEL® material, the entire exterior surface of the solid body 111 includes pores 130 that are interconnected throughout the body. The substrate of the HEDROCEL® carbon-tantalum composite is a skeleton of vitreous carbon, or a reticulated open cell carbon foam, which defines a network of interconnecting pores. The substrate is infiltrated with vapor-deposited thin film of a metallic material. The metallic material is preferably a Group VB transition metal such as tantalum, niobium or alloys thereof.

HEDROCEL® is preferred because it provides the advantages of both metal and ceramic implants without the corresponding disadvantages. HEDROCEL® is well suited for the interbody fusion device of the present invention because it mimics the structure of bone and has a modulus of elasticity that approximates that of human bone. The interconnected porosity encourages bone ingrowth and eliminates dead ends which limit vascularization of the bone. The infiltrated metal film provides strength and stiffness without significant weight increase. A HEDROCEL® implant is sufficiently strong to maintain the intervertebral space and normal curvature of the spine at the instrumented motion segment. At the same time, stress shielding is avoided. This composite material is also advantageous because it eliminates the need for allografts or autografts On additional advantage of this material is that it does not undergo resorption. This prevents early degradation which can inhibit bone regeneration. A non-resorbable implant is also beneficial where complete bone ingrowth may not be achieved. Disadvantages of permanent, non-resorbable implants, however, are avoided because of the excellent biocompatibility and osteoconductivity of the composite.

While HEDROCEL® is preferred, it is contemplated that any suitable high strength porous material may be used. For example, ceramics could be used, such as alumina, zirconia, silicone nitride, carbon, glass, coral, hydroxyapatite, calcium sulfate, ferric calcium phosphorous oxide, zinc calcium phosphorous oxide, calcium phosphate and calcium aluminate ceramics. It is contemplated that calcium phosphate compositions, such as hydroxyapatite, tricalcium phosphate and biphasic ceramics thereof, could be employed if the material could be manufactured to withstand the high spinal loads.

Other metal-open-celled substrate composites are also contemplated. For example, the substrate may be other carbonaceous materials, such as graphite, or ceramics, such as tricalcium phosphate or calcium aluminate. Any suitable metal is contemplated, but Group VB elements, such as tantalum and niobium, and their alloys, are preferred. Tantalum is particularly preferred for its good mechanical properties and biocompatibility.

The interbody fusion devices of this invention can be implanted using an implant driver 50, shown in FIG. 9, according to one aspect of the invention. The implant driver 50 is comprised of a shaft 51 and sleeve 52 concentrically disposed about the shaft. Tongs 54 are formed at one end of the shaft for gripping the interbody fusion device 10 for implantation. The tongs include a tapered outer surface 55 and an opposite flat inner surface 56 adapted to engage the truncated side walls 22 of the interbody fusion device. The tapered outer surface 55 conforms to the root diameter of the interrupted threads 18 so that the tongs 54 essentially complete the full cylindrical shape of the body wall 16. The adaptation of the tong's tapered outer surface 55 facilitates screw insertion of the interbody fusion device 10 since the outer surface 55 will ride within the tapped bore in the vertebral endplates.

Each of the tongs is provided with interlocking fingers 58 and a driving projection 59 extending from the inner surface 56. The function of these components is shown more clearly with reference to FIG. 11. Referring first to FIG. 9, the shaft 51 defines a hinge slot 62 supporting each of the pair of tongs 54. The hinge slot 62 is configured so that the tongs will have a naturally biased position spread sufficiently apart to accept the tapered interbody fusion device 10 therebetween. The shaft 51 defines a conical taper 63 between the hinged slot 62 and each of the tongs 54. This conical taper mates with a conical chamfer 67 defined on the inner wall of the sleeve 52. Thus, as the sleeve 52 is advanced toward the tongs 54, the conical chamfer 67 rides against the conical taper 63 to close or compress the hinge slot 62. In this manner, the tongs 54 are pushed toward each other and pressed into gripping engagement with the interbody fusion device situated between the tongs.

The shaft 51 and sleeve 52 are provided with a threaded interface 65 which permits the sleeve 52 to be threaded up and down the length of the shaft. Specifically, the threaded interface 65 includes external threads on the shaft 51 and internal threads on the sleeve 52 having the same pitch so that the sleeve can be readily moved up and down the implant driver 50. The shaft 51 is also provided with a pair of stops 69 which restrict the backward movement of the sleeve 52 to only the extent necessary to allow the tongs 54 to separate a sufficient distance to accept the interbody fusion device 10.

Figure 11:
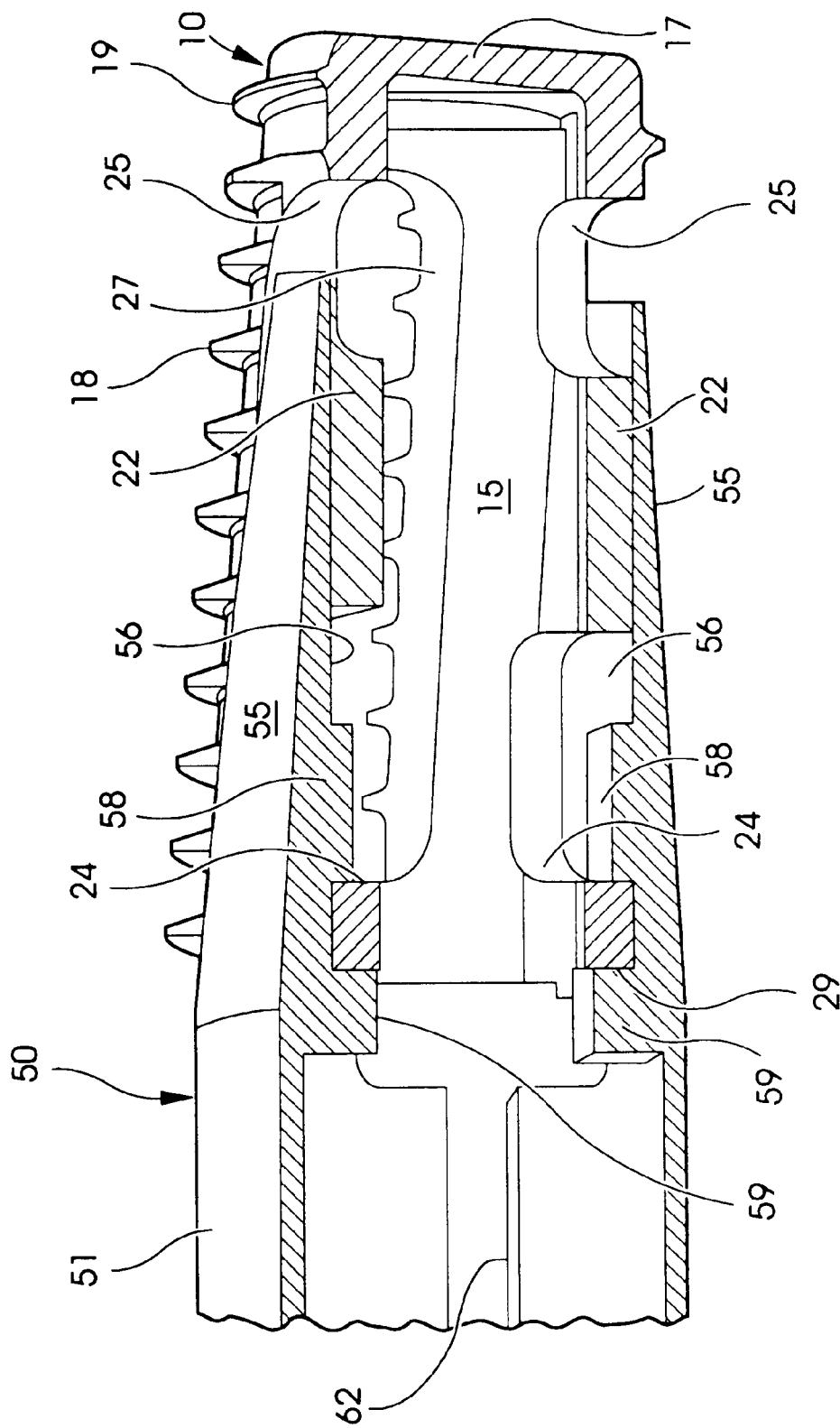
FIG. 11 is an enlarged partial side cross-sectional view showing the implant driver engaging the interbody fusion device, as shown in FIG. 10.

The use of the implant driver 50 is shown with reference to FIGS. 10 and 11. As can be seen in FIG. 10, the outer surface 55 of the tongs 54 reside generally flush with the root diameter of the interrupted threads 18. As seen in FIG. 11, the interlocking fingers 58 can be arranged to fit within the vascularization opening 24 on each of the truncated side walls 22. In a similar fashion, the driving projections 59 engage the driving tool slots 29 at the anterior end 12 of the conical body 11. The combination of the interlocking fingers 58 and driving projections 59 firmly engage the interbody fusion device 10 so that the device can be screw threaded into a tapped or untapped opening in the vertebral bone.

Figure 12:
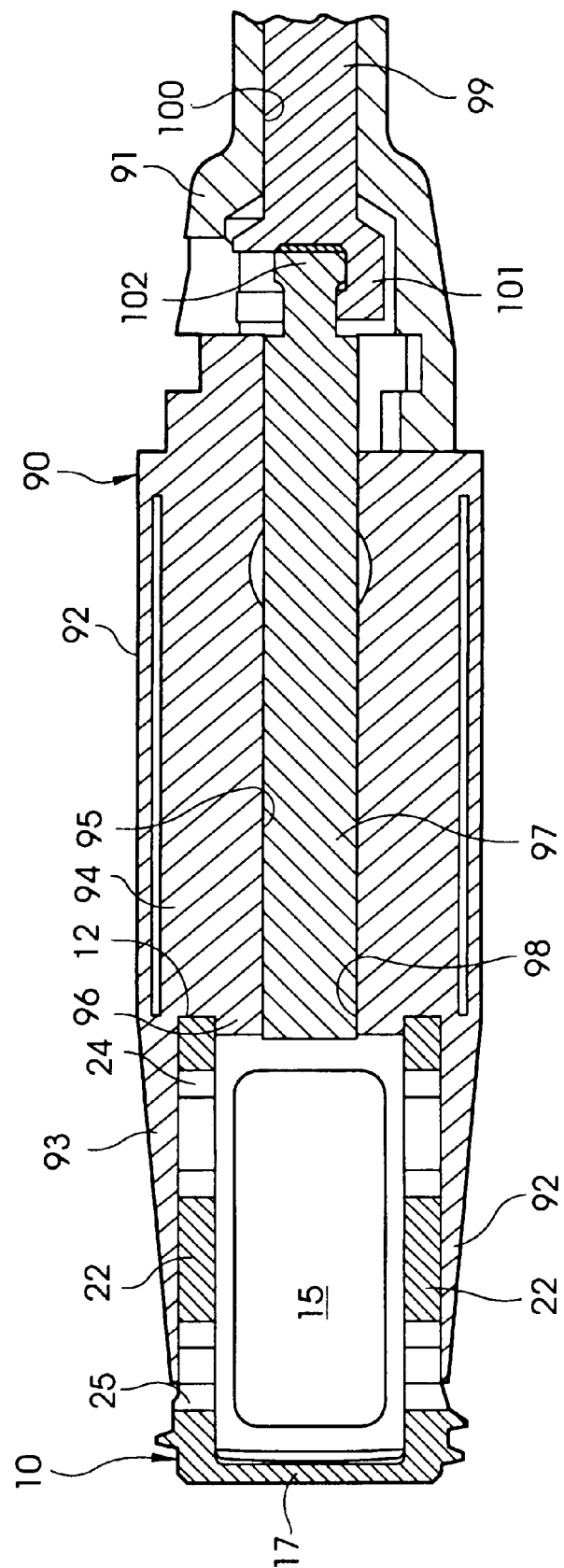
FIG. 12 is an enlarged partial side cross-sectional view showing an implant driver of an alternative embodiment adapted for engaging the interbody fusion device 10.

An alternative embodiment of the implant driver is shown in FIG. 12. The driver 90 includes a shaft 91, having a length sufficient to reach into the intradiscal space from outside the patient. Connected to the end of shaft 91 is a head which defines a pair of opposite tongs 93, each of which are configured for flush contact with the flat truncated side walls 22 of the fusion device 10. Like the tongs 54 of the previously described implant driver 50, the outer surface of the tongs is cylindrical to correspond to the cylindrical threaded portion of the device.

Unlike the implant driver 50, the driver 90 of the embodiment in FIG. 12 uses an expanding collet assembly to firmly grip the fusion device 10 for insertion into the body. Specifically, the head 92 defines a collet 94 having a central collet bore 95 formed therethrough. The collet 94 terminates in an annular flange 96 that at least initially has a diameter slightly smaller than the inner diameter of the fusion device 10 at its end 12. An expander shaft 97 slidably extends through the collet bore and includes a flared tip 98 situated adjacent and extending just beyond the annular flange 96. The flared tip 08 of the expander shaft 97 starts at a diameter sized to slide within the collet bore 95 and gradually flares to a diameter larger than the bore.

The implant driver 90 includes a puller shaft 99 slidably disposed within a bore 100 defined in the shaft 91. The puller shaft 99 has a locking chamber 101 at its end which engages a locking hub 102 formed at the end of the expander shaft 97. The puller shaft 99 projects beyond the end of shaft 91 for access by the surgeon. When the puller shaft 99 is pulled, it pulls the expander shaft 97 away from the annular flange 96 of the collet 94 so that the flared tip 98 becomes progressively engaged within the collet bore 95. As the tip 98 advances further into the bore 95, the annular flange 96 expands from its initial diameter to a larger second diameter sufficient for firm gripping contact with the interior of the fusion device 10. With the fusion device so engaged, the implant driver can be used to insert the device 10 into the surgical site, after which the expander shaft can be advanced beyond the collet bore to release the flared tip and, consequently, the fusion device.

Figure 13A:
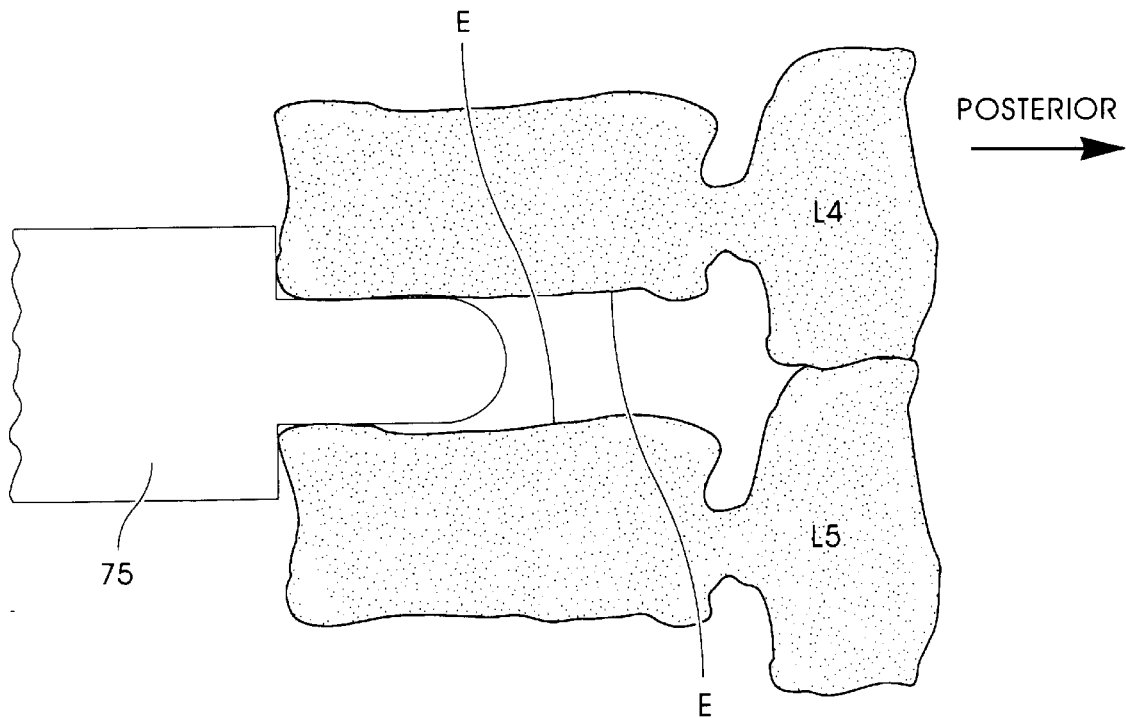
FIGS. 13(a)–13(d) show four steps of a method in accordance with one aspect of the invention for implanting the interbody fusion device, such as the device shown in FIG. 2.
Figure 13B:
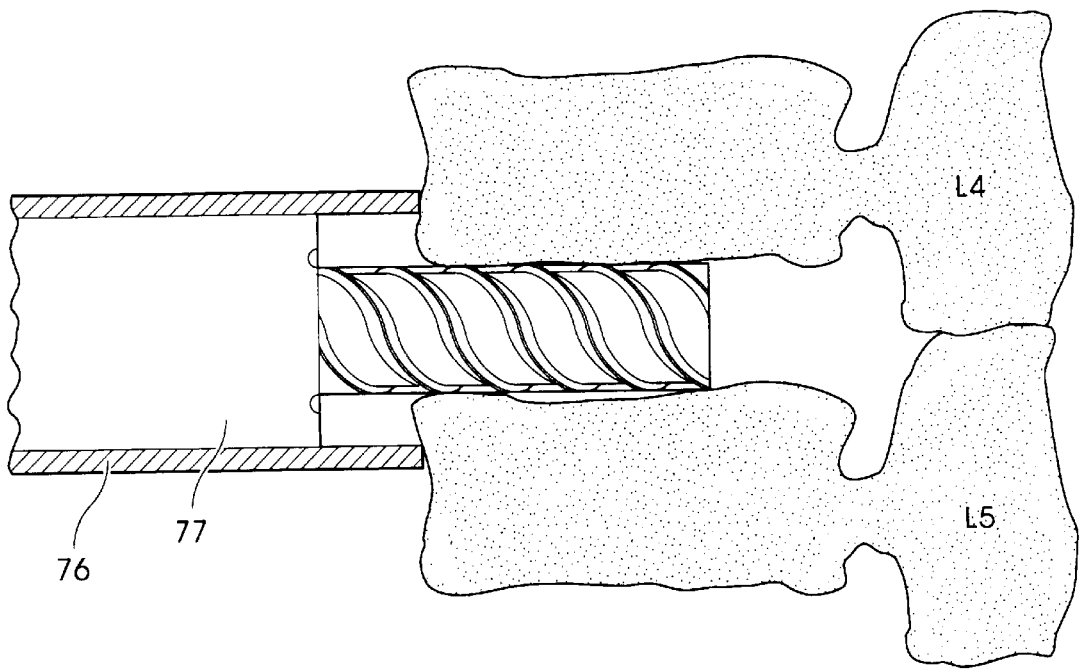

In accordance with the present invention, two methods for implanting the interbody fusion device 10 are contemplated. First, with reference to FIGS. 13(a)–13(d), an anterior approach is shown. As a preliminary step, it is necessary to locate appropriate starting points for implanting the fusion device, preferably bilaterally. In the first step of the anterior approach, a dilator 75 is disposed between the vertebral endplates E to dilate the disc space between the L4 and L5 vertebrae. (It is understood, of course, that this procedure can be applied at other vertebral levels). In the second step, shown in FIG. 13(b), an outer sleeve 76 is disposed about the disc space. The outer sleeve 76 can be of a known design that is configured to positively engage the anterior aspect of the vertebral bodies to firmly, but temporarily, anchor the outer sleeve 76 in position. In essence, this outer sleeve 76 operates as a working channel for this laproscopic-type approach. In this step of FIG. 13(b), a drill 77 of known design is extended through the outer sleeve and used to drill out circular openings in the adjacent vertebral bodies. The openings can be tapped to facilitate screw insertion of the fusion device, although this step is not necessary.

Figure 13C:
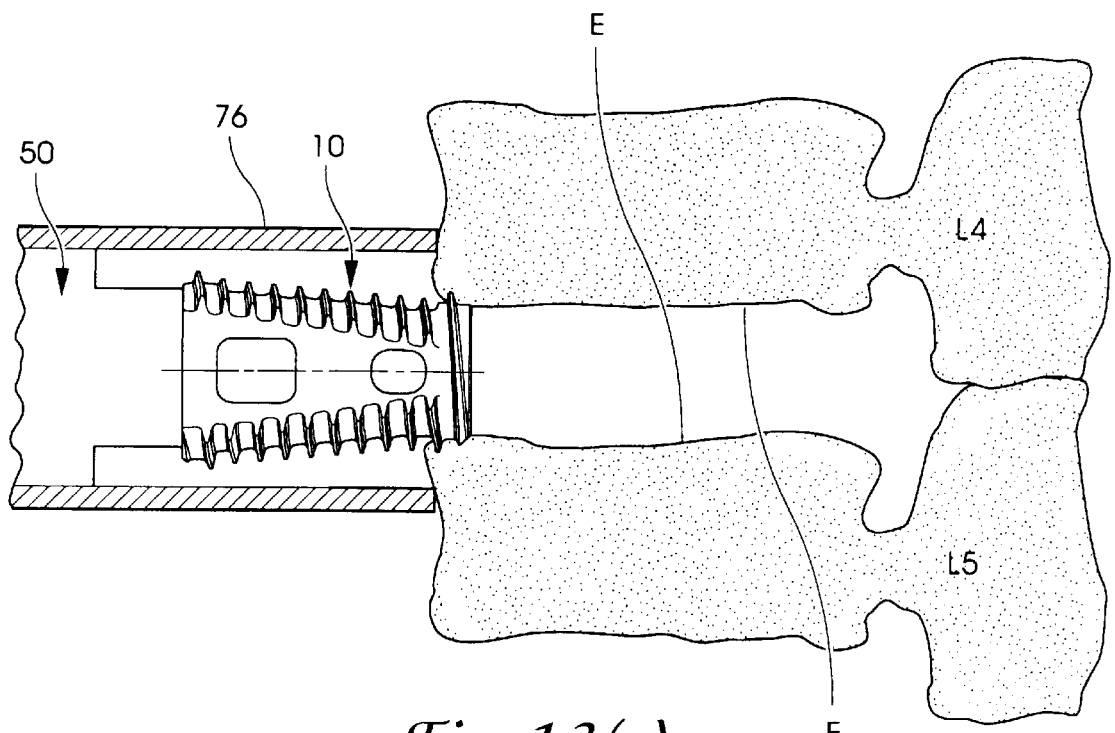
Figure 13D:
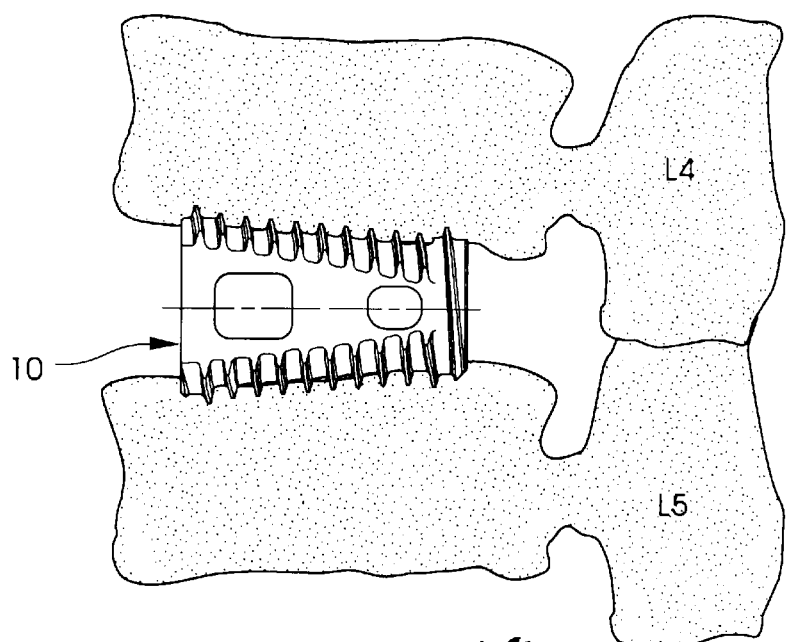

In the next step shown in FIG. 13(c), the fusion device 10 is engaged by the implant driver 50 and extended through the outer sleeve 76 until the starter thread 19 contacts the bone opening. The implant driver 50 can then be used to screw thread the fusion device into the tapped or untapped opening formed in the vertebral endplate E. It is understood that in this step, other suitable driving tools could be used, such as a screw driver type device to engage the driving tool slots 29 at the anterior end 12 of the device 10. As discussed previously, the degree of insertion of the fusion device 10 determines the amount of lordosis added or restored to the vertebral level. In the final step, the implant driver is removed leaving the fusion device 10 in position. It can be seen that once implanted, the closed end wall 17 is directed toward the posterior aspect of the vertebrae. The hollow interior 15 is open at its anterior end, but can be closed by a plastic or metal material, if necessary.

In a second inventive method, as depicted in FIGS. 14(a)–14(d), a posterior approach is implemented. The first two steps of the posterior approach are similar to that of the prior anterior approach, except that the dilator 75, outer sleeve 76 and drill 77 are introduced posteriorly into the instrumented region. This approach may require decortication and removal of vertebral bone to accept the outer sleeve 76. In the third step of this method, the fusion device 10 is inserted through the outer sleeve 76 into the dilated disc space. It is understood that the disc space is dilated only to the extent necessary to receive the implant with the truncated side walls 22 directly facing the vertebral endplates E.

Figure 14A:
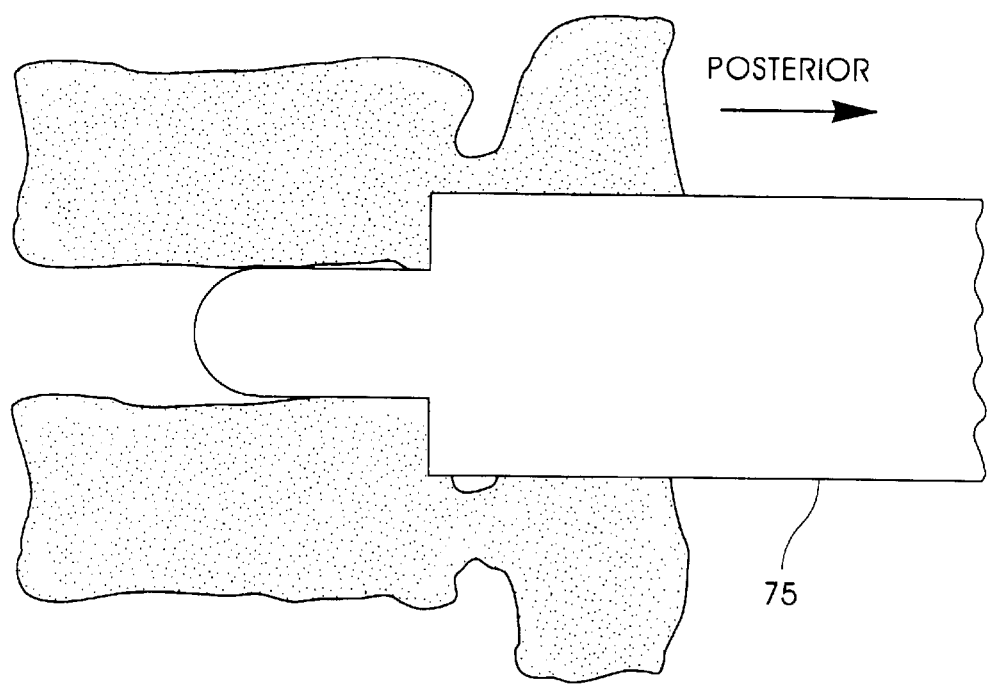
FIGS. 14(a)–14(d) depict steps of an alternative method for implanting the interbody fusion device, such as the device shown in FIG. 2.
Figure 14B:
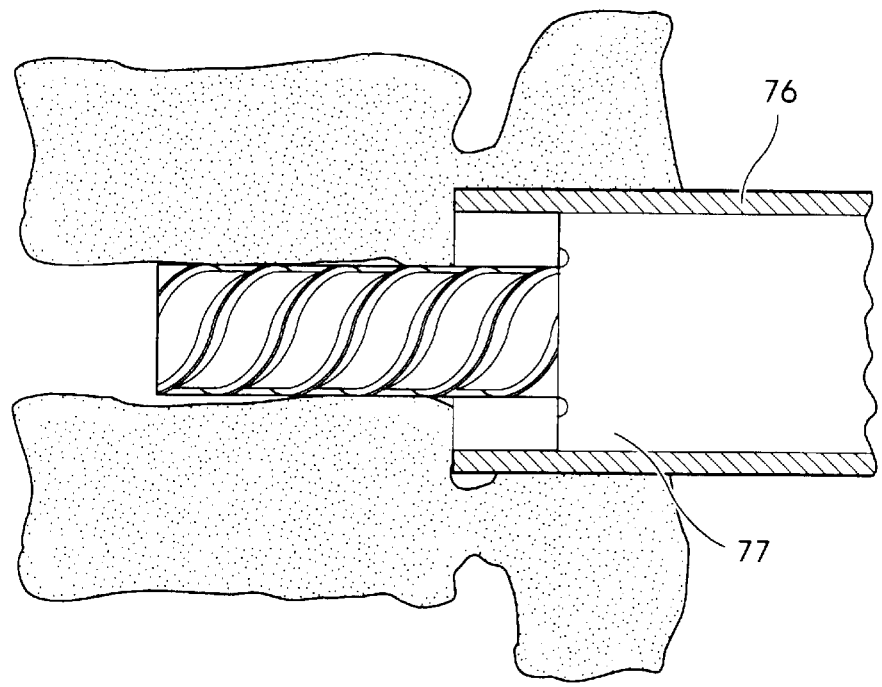
Figure 14C:
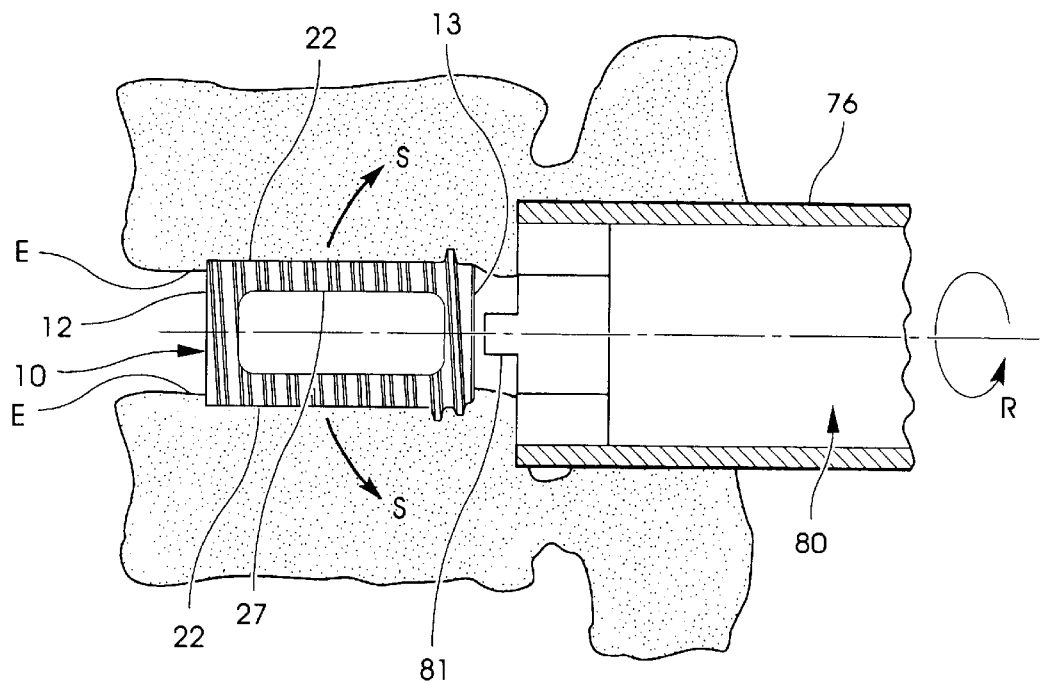
Figure 14D:
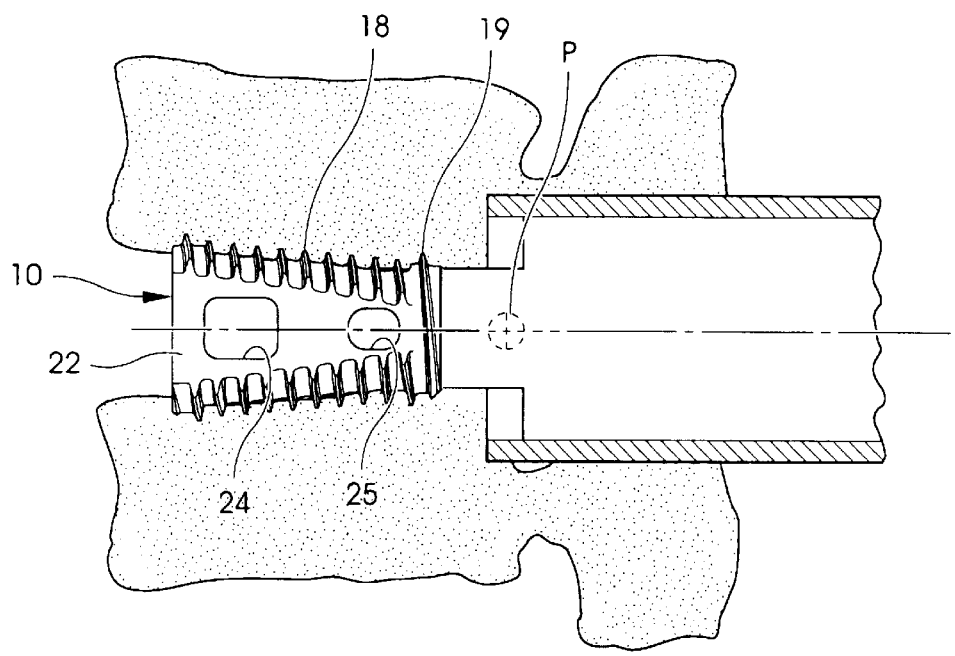

Thus, as shown in FIG. 14(c), the bone ingrowth slot 27 is facing laterally, rather than coronally, as expected for its final implanted position. A suitable driving tool 80 can be provided to project the fusion device 10 through the outer sleeve 76 and into the intradiscal space. In one embodiment, the driving tool 80 includes a projection 81 which is configured to engage a slot opening formed in the end wall 17 at the posterior end 13 of the fusion device 10. An internal thread (not shown) can be used to fix the device 10 to the driver 80.

Once the fusion device 10 has been advanced into the intradiscal space to the appropriate depth relative to the pivot axis P of the vertebrae, the driving tool 80 is used to rotate the implant in the direction of the rotational arrow R in FIG. 14(c). As the driving tool 80 is rotated, the device itself rotates so that the interrupted threads 18 start cutting into the vertebral b one at the endplates E. In this manner, the implant operates as a cam to separate the adjacent vertebrae in the direction of the spreading direction arrows S in FIG. 14(c). This camming approach provides a somewhat easier insertion procedure in that a single rotation is required to lock the implant into the vertebral bone. In contrast, the formerly discussed screw insertion technique requires continuous threading of the device into position.

With either technique, the position of the fusion device 10 with respect to the adjacent vertebrae can be verified by radiograph or other suitable techniques for establishing the angular relationship between the vertebrae. Alternatively, the preferred depth of insertion of the implant can be determined in advance and measured from outside the patient as the implant is positioned between the vertebrae.

It can be seen that the interbody fusion device 10, implant driver 50 and techniques of the present invention provide significant advantages over the prior devices and techniques. Specifically, the fusion device 10 provides a hollow threaded implant that maximizes the potential for bony fusion between adjacent vertebrae, while maintaining the integrity of the implant itself. It is understood that the spine endures significant loads along its axial length, which loads must be supported by the fusion device 10 at least until solid fusion is achieved. The device 10 also provides means for vascularization and tissue ingrowth to occur which speeds up the fusion rate and enhances the strength of the resulting fused bony mass. Another significant aspect is that the tapered shape of the implant allows the surgeon to restore and maintain the proper curvature or relative angle between vertebral bodies. This avoids the significant problems associated with prior devices in which product deformities arise and the spine goes out of balance. A further advantage achieved by the device and its implant driver is the capability for insertion either anteriorly or posteriorly using a laproscopic approach. Depending upon the vertebral level, either approach may be preferred, so it is important that the implant be adapted for insertion from either direction. Controlled insertion of the device is provided by the screw-in technique used for anterior insertion (vs. pounding in) and for the slide-in and cam method used for the posterior technique.

During a surgical implantation procedure, the surgeon may apply an osteogenic material to a fusion device 10 or 30 by packing the hollow interior 15 with an osteogenic material. Alternatively, in the case of a fusion device such as device 30 or 110, the osteogenic material can be applied by introducing an osteogenic composition to the pores of the bone ingrowth material. Any suitable osteogenic material or composition is contemplated. The osteogenic compositions preferably comprise a therapeutically effective amount of a bone inductive factor such as a bone morphogenetic protein in a pharmaceutically acceptable carrier.

For the osteogenic compositions, any suitable carrier which provides a vehicle for introducing the osteogenic material into the pores of the bone ingrowth material or the hollow interior of the device is contemplated. Such carriers are well known and commercially available. The choice of carrier material is based on biocompatibility, biodegradability, mechanical properties and interface properties. The particular application of the compositions of the invention will define the appropriate formulation. The carrier may be any suitable carrier capable of delivering the proteins to the implant. Most preferably, the carrier is capable of being resorbed into the body. One preferred carrier is an absorbable collagen sponge marketed by Integra LifeSciences Corporation under the trade name Helistat® Absorbable Collagen Hemostatic Agent. Another preferred carrier is an open cell polylactic acid polymer (OPLA). Other potential matrices for the compositions may be biodegradable and chemically defined calcium sulfate, tricalcium phosphate (TCP), hydroxyapatite (HA), biphasic TCP/HA ceramic, polylactic acids and polyanhydrides. Other potential materials are biodegradable and biologically well defined, such as bone or dermal collagen. Further matrices are comprised of pure proteins or extracellular matrix components. The osteoinductive material may also be an admixture of the osteoinductive cytokine and a polymeric acrylic ester carrier. The polymeric acrylic ester can be polymethylmethacrylic.

Figure 16:
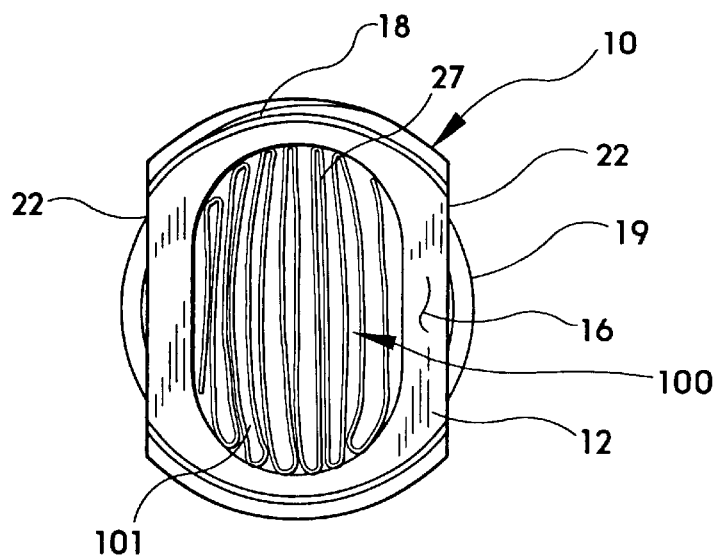
FIG. 16 is an end elevational view of the interbody fusion device shown in FIG. 15.
Figure 15:
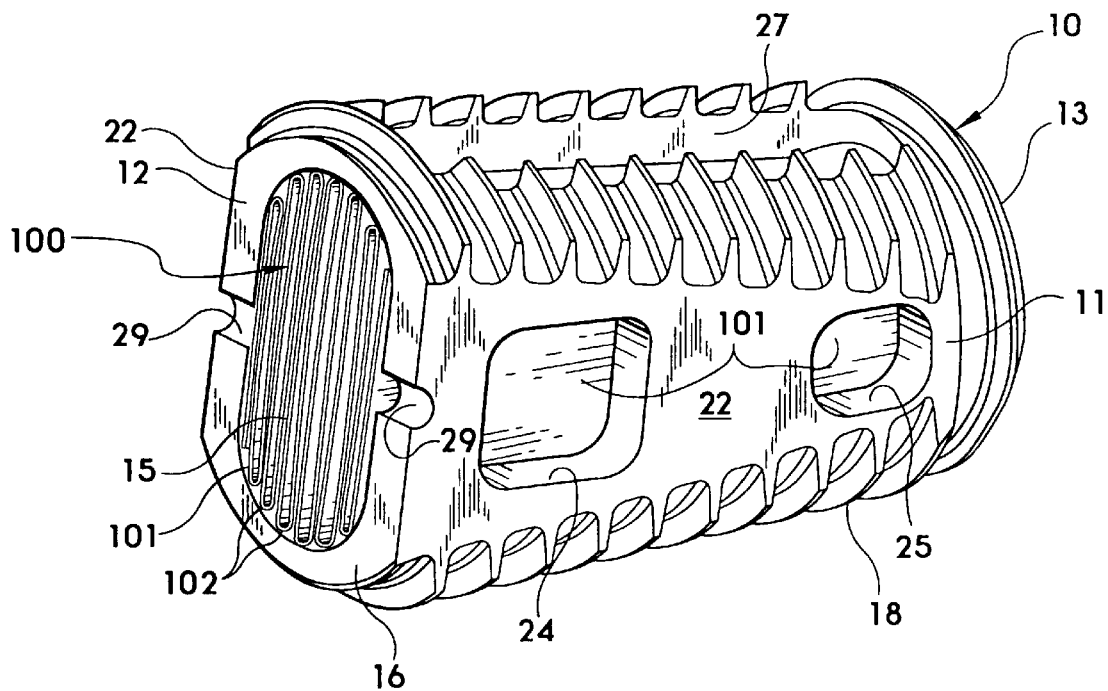
FIG. 15 is an enlarged perspective view of an interbody fusion device having an osteogenic material in the hollow interior according to one embodiment of the present invention.

For the hollow fusion devices, such as device 10, the carriers can be provided in strips or sheets which may be folded to conform to the hollow interior 15 as shown in FIGS. 15 and 16. It may be preferable for the carrier to extend out of openings of the devices, such as the vascularization openings 24, 25, to facilitate contact of the osteogenic material with the highly vascularized tissue surrounding the vertebrae. In one embodiment, the osteogenic material 100 includes a polylactic acid polymer acting as a carrier for a bone morphogenetic protein, such as BMP-2. In this specific embodiment, the osteogenic material 100 is in the form of a sheet 101 that is overlapped at folds 102 within the hollow interior 15 of the device 10. Preferably, the sheet 101 is long enough so that when it is folded within the device 10 it substantially completely fills the hollow interior and extends at least partially into the vascularization openings 24 and 25.

As shown in FIGS. 15 and 16, the sheet 101 is folded generally parallel with the truncated side walls 22 so that the folds 102 of the sheet 101 are disposed adjacent the slots 27 in the threaded portion of the device. Alternatively, the sheet 101 can be folded so that the layers between the folds are generally perpendicular to the side walls 22. In this instance, the sheet 101 may extend at least partially into the slots 27.

The osteogenic material 100 can also be provided in several strips sized to fit within the hollow interior 15 of the fusion device 10. The strips (not shown) can be placed one against another to fill the interior. As with the folded sheet 101, the strips can be arranged within the device 10 in several orientations, such as with the surface of the strips directed either toward the vascularization openings 24, 25 or toward the slots 27. Preferably, the osteogenic material 100, whether provided in a single folded sheet or in several overlapping strips, has a length corresponding to the length of the hollow interior 15 of the device 10 and a width corresponding to the width of the device transverse to its longitudinal axis.

As discussed in the Kaplan patent, the open cell tantalum material provides highly interconnected three-dimensional porosity that encourages bone ingrowth. Kaplan type materials facilitate bone ingrowth throughout the entire device for complete fusion and have the strength of metal without the disadvantages of metal such as stress shielding and incomplete fusion. An additional benefit of the porosity of these materials is that a bone growth inducing composition can be introduced into the pores. For example; in one embodiment, the composition includes a bone morphogenetic protein in a liquid carrier which can be introduced into the pores to promote fusion. BMPs have been found to significantly reduce the time required to achieve arthrodesis and fusion across an instrumented disc space. Most preferably, the bone morphogenetic protein is a BMP-2, such as recombinant human BMP-2. However, any bone morphogenetic protein is contemplated including bone morphogenetic proteins designated as BMP-1 through BMP-13. BMPs are commercially available from Genetics Institute, Inc., Cambridge, Mass. and may also be prepared by one skilled in the art as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al.

The BMP may be provided in freeze-dried form and reconstituted in sterile water or another suitable medium or carrier. The carrier may be any suitable medium capable of delivering the proteins to the implant. Preferably the medium is supplemented with a buffer solution as is known in the art. The bone growth inducing composition can be introduced into the pores in any suitable manner. For example, the composition may be injected into the pores of the implant. In other embodiments, the composition is dripped onto the biocompatible material or the biocompatible material is soaked in the composition. In one specific embodiment of the invention, rhBMP-2 is suspended or admixed in a liquid carrier, such as water or liquid collagen. The liquid can be dripped into the device or the device can be immersed in a suitable quantity of the liquid, in either case for a period of time sufficient to allow the liquid to invade all of the interconnected pores throughout the pore material of the device.

In some cases, a BMP-bonding agent is applied to the porous biocompatible material of the implant prior to introduction of the BMP so that the agent can coat the pores of the device. Preferably, the agent is a calcium phosphate composition. It has been discovered that the rate of delivery of bone morphogenetic proteins to the fusion site can be controlled by the use of such agents. The calcium phosphate compositions are thought to bond with the bone morphogenetic protein and prevent the BMP from prematurely dissipating from the device before fusion can occur. It is further believed that retention of the BMP by the agent permits the BMP to leach out of the device at a rate that is conducive to complete and rapid bone formation and ultimately, fusion across the disc space. Any suitable, biocompatible calcium phosphate composition is contemplated. In a preferred embodiment, a layer of hydroxyapatite several microns thick is applied to the Kaplan material. The hydroxyapatite covers the tantalum film-covered ligaments while leaving the pores open. Also contemplated are tricalcium phosphate ceramics and hydroxyapatite/tricalcium phosphate ceramics.

The calcium phosphate composition may be applied to the porous biocompatible material of the implant in any suitable manner such as plasma spraying or chemical dipping where the porous material is dipped into a slurry of calcium phosphate composition. Methods for applying a coating of calcium phosphate compositions are described in the following: U.S. Pat. No. 5,164,187 to Constantz.et al., U.S. Pat. No. 5,030,474 to Saita et al, U.S. Pat. No. 5,330,826 to Taylor et al, U.S. Pat. No. 5,128,169 to Saita et al, Re. 34,037 to Inoue et al, U.S. Pat. No. 5,068,122 to Kokubo et al, and U.S. Pat. Nos. 5,188,670 and 5,279,831 to Constantz which are hereby incorporated by reference.

For hollow spacers, such as the one depicted in FIG. 2, this invention provides a cap 300 (FIG. 17) for blocking the opening 15a to prevent expulsion of graft material within the chamber 15. (See FIG. 18.) In preferred embodiments, the cap 300 includes an occlusion body 301 sized and shaped for contacting and closing the opening 15a and an elongate prong or anchor 310 projecting from the body 301.

Figure 17:
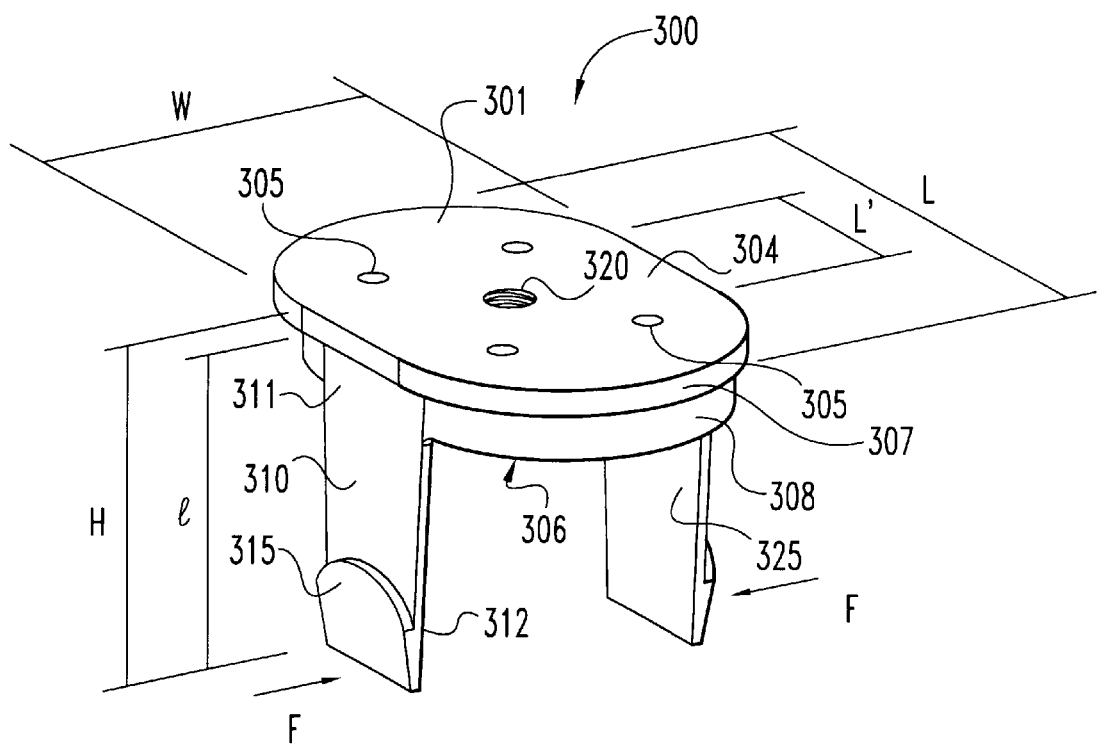
FIG. 17 is a perspective view of a cap according to this invention.

In the embodiment shown in FIG. 17, the occlusion body 301 includes an outer wall 304, an opposite inner surface 306 and a flange 307 in communication with and connected to the outer wall 304. The flange 307 defines an engaging surface 308 for contacting the internal surface of the body wall 16 of the load bearing body 11'. The flange 307 also prevents the cap 300 from traveling into the interior of the fusion device.

Figure 18:
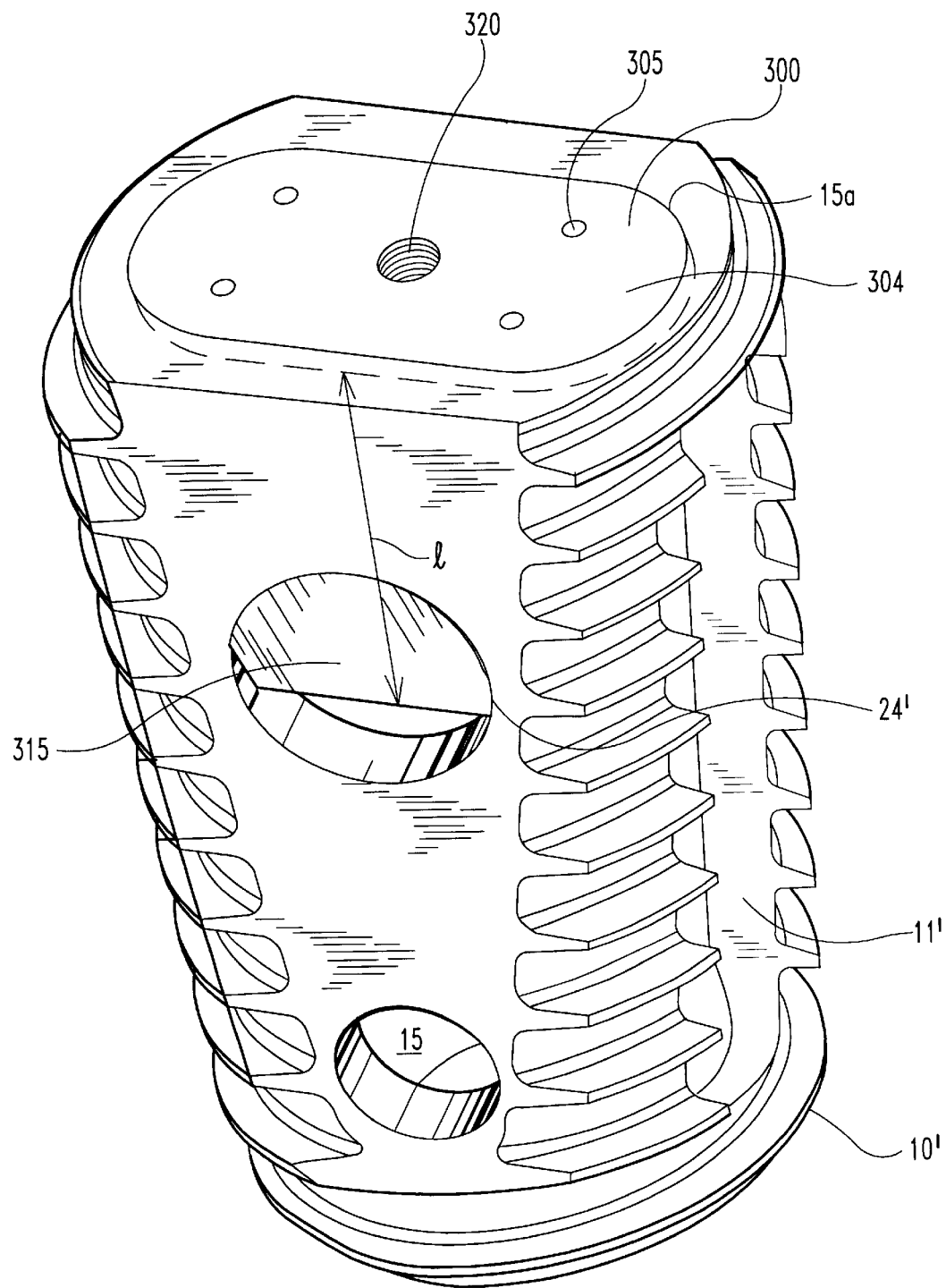
FIG. 18 is a side perspective view of a fusion device of this invention with the cap depicted in FIG. 17.

The anchor 310 includes a first end 311 attached to the occlusion body 301 and an opposite second end 312 having engaging means for engaging the load bearing body 11' to hold the occlusion body 301 within the opening 15a. In a preferred embodiment, the engaging means is a lip 315 projecting from the second end 312 which contacts the internal surface of the load bearing body 11'. Preferably the anchor 310 has a length 1 which reaches from the occlusion body 301 to a body wall aperture when the cap 300 is inserted into the opening 15a. In FIG. 18, the lip 315 is engaged to a vascularization opening 24'. In some embodiments, the outer wall 304 of the cap 300 will preferably be flush or nearly flush with the opening 15a as shown in FIG. 18 for a low profile device.

The cap 300 shown in FIG. 17 also includes a second, opposite elongate anchor 325 projecting from the occlusion body 301. It is of course contemplated that any number of anchors could be provided. The anchors are preferably composed of a resilient material, particularly when more than one anchor is provided. The resilient material allows the anchors 310, 325 to be slightly deflected by an inward force F for insertion. Once the cap 300 is inserted into the opening 15a the force on the anchors 310, 325 is released allowing the anchors 310, 325 to return to their normal configuration in which the anchors 310 engage the load bearing body 11'.

Any suitable material is contemplated for the caps of this invention, such as biocompatible metals and polymers. In one preferred embodiment, the cap is composed of titanium. In another preferred embodiment the cap is polymer, such as for example, polyethylene, polyvinylchloride, polypropylene, polymethylmethacrylate, polystyrene and copolymers thereof, polyesters, polyamides, fluorocarbon polymers, rubbers, polyurethanes, polyacetals, polysulfones and polycarbonates. Biodegradable polymers, including, for example, glycolide, lactide and polycarbonate based polymers, are also contemplated for the cap. Such polymers could be manufactured to degrade after the expected incorporation/degradation of the graft material or graft substitute. Polyethylene is particularly preferred because it is inert and provides a smooth, nonirritating surface. Another benefit is that polyethylene is radiolucent and does not interfere with radiological visualization. Other suitable materials include stainless steel and HEDROCEL®.

The cap also preferably includes osteogenic apertures 305 defined through the outer wall 304 which are sized to permit bone ingrowth and protein egress. The osteogenic apertures 305 are particularly preferred;when a material such as polyethylene is chosen for the cap. Such biocompatible polymers are not known to allow bony attachments as do other materials such as titanium. Therefore, a solid plastic cap could impede bone formation in the area of the cap. The osteogenic apertures are also advantageous because they facilitate controlled diffusion of bone growth proteins implanted within the chamber to facilitate bony bridging and fusion around the device. The resulting fusion around the device supplements the device ingrowth fusion mass within the device for a more solid overall fusion. The bony bridging around a device is also favorable because it serves as a better indicator of the success of the procedure. Bone ingrowth within a device is difficult to assess using plain film radiographs but bony bridging outside a device can be easily visualized.

Any suitably sized cap is contemplated. The dimensions of the caps will vary as needed to effectively block the openings of fusion devices. Referring now to FIG. 17, one cap has a length L (of the occlusion body including the flange) of 0.548 inches (13.7 mm), a length L' of the occlusion body without the flange of 0.488 inches (12 mm), a width W of 0.330 inches (8.25 mm) and a height H of 0.377 inches (9.4 mm).

This invention also provides tools for manipulating caps for interbody fusion devices. The tools include means for engaging the cap and means for engaging the fusion device for inserting and removing a cap. During a surgical procedure, the cap 300 could be inserted into the opening 15a after the fusion device 10' is implanted and the chamber is packed with osteogenic material. In some cases it may be necessary to remove a cap during or after the surgery to replace or remove the osteogenic material in the chamber or to access the fusion device for revision. The cap 300 shown in FIG. 17 includes a tool hole 320 for receiving an insertion or removal tool. The hole 320 is preferably threaded but any suitable engagement surface, such as an internal hex or the like, is contemplated.

One embodiment of a tool 400 of this invention is depicted in FIGS. 19 and 20. The tool 400 includes a pair of prongs 401 each having a proximal end 402 defining first engaging means for engaging the fusion device and a shaft 410 having a first end 411 defining second engaging means for engaging a cap. The tool also includes means for slidably supporting the shaft 410 between the prongs 401. In one embodiment, the invention includes a body or housing 420 defining a passageway 421 therethrough. The distal end 403 of the prongs 401 are attached to the housing 420 in this embodiment. As depicted in FIG. 20, the prongs 401 can be attached to the housing 420 with screws 404. Of course any suitable fastening means is contemplated.

Figure 21:
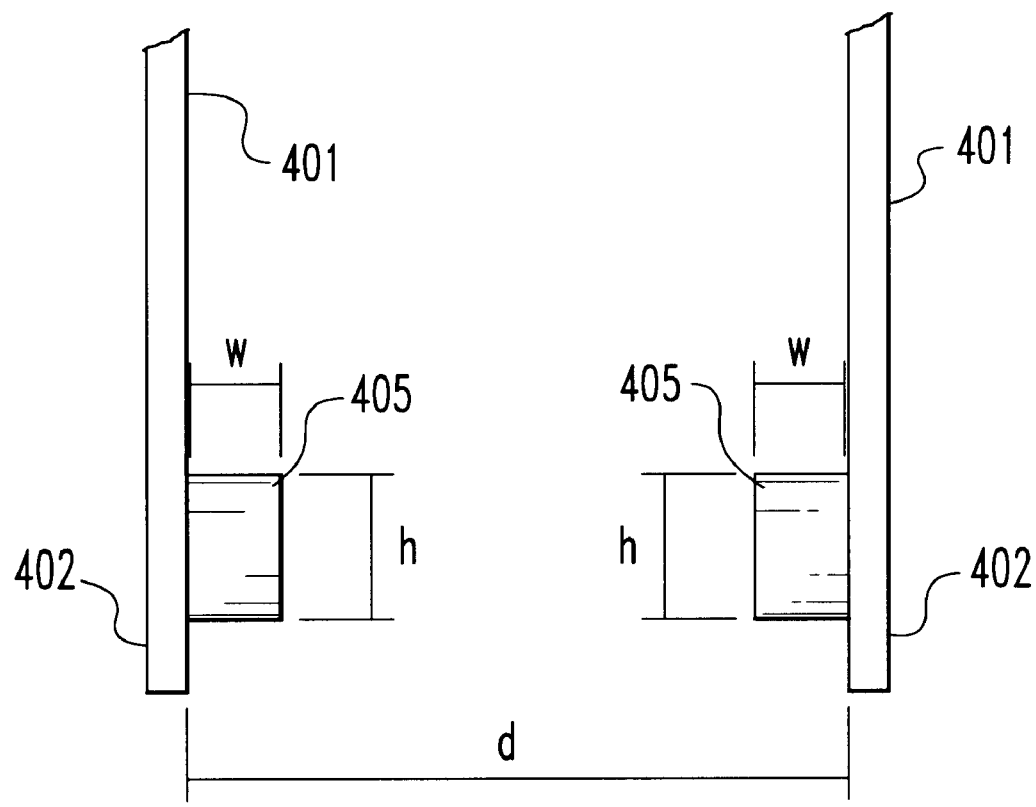
FIG. 21 is an enlarged view of a portion of the tool of FIG. 19.

The prongs 401 can be used to steady the fusion device for insertion of the cap or can be used to engage the fusion device and/or the cap for removal of the cap. In the embodiment depicted in FIG. 19, the proximal end 402 of the prongs 401 includes facing engagement surfaces 404 for engaging the fusion device. In a most preferred embodiment, a pair of releasing members 405 are disposed on each of the facing engagement surfaces 404. Referring now in particular to FIG. 21, the releasing members 405 have a height h and a width w for being insertable into apertures 24' in a fusion device 10'. The tool of FIGS. 19–21 can be used to remove a cap 300 of this invention which is inserted into the opening 15a of a fusion device 10' as shown in FIG. 18. The releasing members 405 are insertable into the apertures 24' for applying pressure F to elongate arms or anchors 310 of the cap 300 to deflect the anchors 310 inwardly to release the cap 300 from the interbody fusion device 10'. In embodiments where the anchors 310 include a lip 315 or other engaging means, the releasing members 405 are insertable into the apertures 24' to disengage the lips 315 from the apertures.

The distance d between the proximal ends 402 of the prongs 401 is preferably adjustable to facilitate engaging portions of the fusion device and/or cap. In a preferred embodiment this is accomplished by composing the prongs 401 of a resilient material such as stainless steel. The adjustable feature could be obtained by other means such as by providing a hinge at the distal end 403 of the prongs 401. Any other such suitable means of adjusting the distance d are contemplated.

Referring again to FIG. 19, the first end 411 of the shaft 410 defines a cap-engaging tip 415 configured for matingly engaging a tool hole in the cap. In the embodiment shown in FIG. 19, the cap engaging tip 415 defines threads for engaging a threaded tool hole in a cap 300 as shown in FIG. 22. Any suitable tool engaging means is contemplated such as, for example, a hex for engaging an internal hex in a cap.

Figure 23:
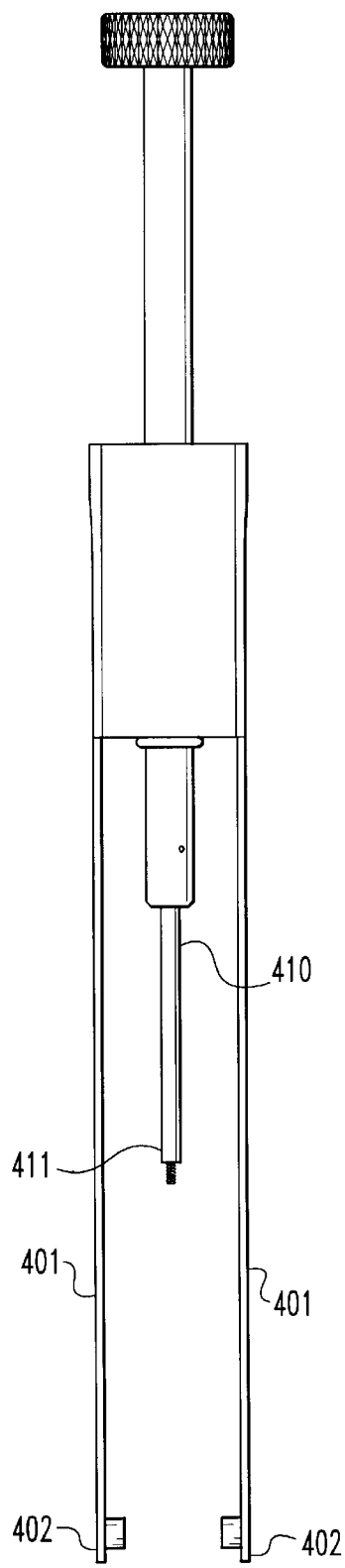
FIG. 23 is a side elevational view of the tool of FIG. 19 in a retracted position.
Figure 24:
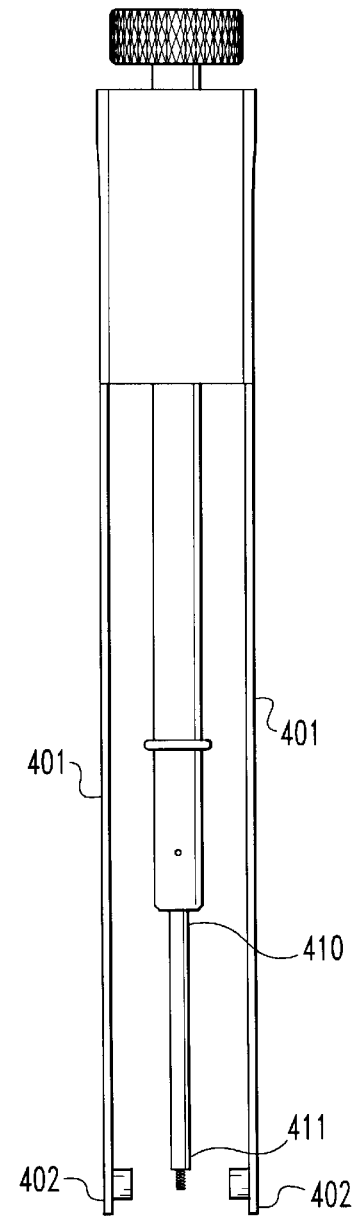
FIG. 24 is a side elevational view of the tool of FIG. 19 in an extended position.

In the embodiment shown in FIGS. 19–22, the shaft 410 is slidably disposed within the passageway 421 of the housing 420. The shaft 410 is slidable between a retracted position (FIG. 23) and an extended position (FIG. 24) at which the first end 411 is adjacent and between the proximal ends 402 of the prongs 401. To insert a cap into a fusion device, the prongs 401 can be used to engage and hold the fusion device. The engaging end 415 engages a tool hole of the cap and the cap is delivered to the fusion device by sliding the shaft 410 to the extended position (FIG. 24). Where the engaging end 415 is threaded, the shaft 410 is unscrewed from the cap by rotating the shaft 410 within the housing 420 after the cap is inserted into the fusion device. To remove a cap, the prongs 401 are first engaged to the fusion device. The prongs 401 may engage a body wall of the device. When used with a cap 300 such as depicted in FIGS. 17 and 18, the releasing members 405 are inserted into the apertures 24' to disengage the lips 315 and deflect the anchors 310, 325 inwardly. The shaft 410 is then moved from the retracted position (FIG. 23) to the extended position (FIG. 24) and then rotated to engage the tool engaging hole 320 of the cap 300. The shaft is then returned to the retracted position (FIG. 23) with the cap 300 engaged to the engaging end 415.

In the embodiment depicted in FIG. 19 the first end 411 of the shaft 410 is a metal rod 412 attached to an autoclavable plastic center rod 413. An autoclavable plastic is chosen for a light weight yet reusable device. In one embodiment, the metal rod 412 is press fit into the plastic center rod and is further engaged by a pin 414.

In one embodiment the center rod 413 of the shaft 410 is slip fit into the passageway 421 of the housing 420. Proximal and distal stop members are preferably provided to prevent the shaft 410 from sliding out of the housing 420. A proximal stop member is preferably disposed on the center rod 413 adjacent the first end 411 for preventing the first end 411 from entering the passageway 421. As shown in FIG. 19, the proximal stop member is an O-ring 430 engaged to the center rod 413 of the shaft 410. In one embodiment, the center rod 413 defines a groove 431 (FIG. 25) for seating the O-ring 430. The groove 431 is positioned so that when an O-ring 430 is seated therein the shaft 410 cannot move beyond the retracted position shown in FIG. 23 to prevent the first end 411 from entering the passageway 421.

A distal stop member 440 may be attached to the second end 416 of the shaft 410 which has a perimeter that is larger than a perimeter of the passageway 421 to prevent the second end 416 from entering the passageway 421. As shown in FIG. 25, where the stop member 440 and passageway 421 are circular, the distal stop member 440 has a diameter $D_1$ which is larger than a diameter $D_2$ of the passageway 421.

The tools of this invention are also preferably provided with a distal shaft manipulating member attached to the second end 416 of the shaft 410 for rotating and sliding the shaft 410 within the passageway 421. In the embodiment shown in FIG. 19 the manipulating member is thumb wheel 441. Thumb wheel 441 has a dimension or diameter $D_1$ that is larger than diameter $D_2$ and therefore also is the distal stop member 440.

To promote a further understanding and appreciation of the invention, the following specific examples are provided. These examples are illustrative of the invention and should in no way be construed as limiting in nature.

EXAMPLE 1

Surgical Technique: Twenty-one mature female Alpine goats were used in this study. The goats weighed between 42 and 62 kilograms. All the goats underwent a surgical procedure under general endotracheal anesthesia using intravenous valium and ketamine for induction, and inhalation halothane for maintenance anesthesia. The anterior neck was prepped in a sterile fashion and a right anterolateral approach to the cervical spine was carried out through a longitudinal skin incision. The well developed longus coli muscle was incised in the midline, and the disc spaces at C2–C3, C3–C4, and C4–C5 exposed. Anterior cervical discectomies were carried out at each level by first excising the soft disc. An 8 mm distraction plug centered on a post was then tapped into the disc space providing distraction of the space. A working tube was then passed over the post and prongs at the end of the tube tapped into the vertebral bodies above and below the disc space. These prongs maintained distraction of the disc space as the centering post and distraction plug were removed. The disc space and vertebral bodies/endplates were then reamed with a 10 mm reamer through the working tube. The bone reamings were saved and used as graft materials. The reamed channel was then tapped followed by insertion of a 10 millimeter-diameter titanium BAK device (SpineTech, Minneapolis, Minn.). No attempt was made to excise the posterior longitudinal ligament or expose the spinal canal.

The goats were divided into three treatment groups consisting of seven goats each. Group I had a device filled with autogenous bone graft harvested from the reamings at each disc level. Group II utilized a hydroxyapatite-coated implant filled with autogenous bone reamings as graft. Group III utilized a device filled with a collagen sponge impregnated with 200 μg of recombinant BMP-2 (Genetics Institute, Cambridge, Mass.). Prior to installation of the devices, wounds were irrigated with a solution of normal saline, bacitracin (50U/cc), polymyxin B (0.05 mg/cc), and neomycin (0.5%). The longus coli muscle was then closed with a running suture. The subcutaneous tissue was reapproximated with interrupted sutures and the skin with a running suture.

Post-operatively the animals were maintained under observation until fully recovered from general anesthesia. They received two doses of Naxcell (ceftiofur), 500 mg intravenously properatively and 500 mg intramuscularly post-operatively. A soft bandage was applied to the animals neck, and they were allowed ad lib activity under daily observation in a pen for several days.

Clinical evaluation was performed every three weeks. Lateral cervical spine radiographs were obtained immediately post-operatively and at three, six and nine weeks. Fluorochrome labels.were administered at three, six and nine weeks. These consisted of oxytetracycline (30 mg/kg IV) at three weeks, alizarin complex one (30 mg/kg IV) at six weeks, and DCAF (20mg/kg IV) at nine weeks. At twelve weeks, the goats were euthanized by an intravenous injection of Beuthanasia. The cervical spine was then excised, and all surrounding tissues removed from it. The specimen was then radiographed in the AP and lateral planes.

Biomechanical Testing: The spine specimens were brought fresh to the biomechanics laboratory for biomechanical testing. The spines were mounted into frames at C2 and C7 with a polyester resin (Lite Weight 3 Fiberglass-Evercoat, Cincinnati, Ohio). The biomechanical tests were performed on a modified MTS Bionix 858 Servo-Hydraluic Material Tester (MTS Corporation, Minneapolis, Minn.). The MTS machine can apply axial compressive and torsional loads about the longitudinal axis of the spine. This system allows a constant bending moment to be applied uniformly over the length of the spine resulting in a pure sagittal flexion and extension load, with axial load and torsion maintained at zero.

Separate tests were performed for axial compression, torsion, flexion-extension, and lateral bending. Axial load was cycled from 0 to 100 N in compression. Coupled motion in rotation or sagittal bending was allowed. Torsion was cycled from positive to negative 5N–m with a 50 N compressive preload. Again, coupled motion was allowed by leaving axial load and sagittal bending in load control. Sagittal bending was cycled from flexion to extension with a uniform 2 N–m bending moment with a 5 N tensile preload. Lateral bending was performed from left to right with a uniform 2 N–m bending moment with a 5 N tensile preload. Each test consisted of five sinusoidal load cycles at 0.1 Hz. Specimens were preconditioned over the first four cycles with data from the fifth cycle used for analysis. Data acquisition was continuous throughout each test and stored in a computer data file.

Axial compressive data included axial load (N) and axial displacement (mm). Flexion-extension, torsional, and lateral bending data included axial load (N), torque (N–m), and rotational displacement (degrees). The measurement of axial, flexion-extension, lateral bending and torsional displacement was performed simultaneously using extensometers applied across each of the operated disc levels. Data analysis consisted of stiffness calculation across each disc space for axial load, flexion-extension, torsion, and lateral bending.

Radiographic Analysis: Analysis was carried out on all of the three, six, nine and twelve week radiographic films. The radiographs were analyzed for cage migration and the absence or presence of lucent lines surrounding each cage. If a lucent line was seen on either the AP or lateral radiograph, that cage was noted to possess a lucency.

Histologic Analysis: Following biomechanical testing specimens were removed from the mounting grips and frames. The spines were cut through the mid-axial portion of the C3-, C4, and C6 vertebral bodies thus providing three individual specimens containing the implant in a bone-disc space-bone block. The specimens were then cut into sagittal sections starting on the right lateral side using an Isomet Plus precision saw (Buehler Instruments, Lake Bluff, Ill.). When the sagittal slice revealed the first sign of the cage, two additional 2.5 mm slices were removed. These two slices were then stores in 70 percent alcohol awaiting microradiographic analysis. A third sagittal slice was then removed and set aside for fluorochrome analysis. The remaining specimen is stored in 70 percent alcohol.

The first two slices that contain the cage were then processed for microradiographs. A sagittal microradiograph was obtained in a Hewlett Packard Faxitron unit (Hewlett Packard, McMinnville, Ore.). Each sagittal microradiograph contained two cage-vertebral body interfaces. Each of these interfaces was graded separately and as to whether or not there was bone or fibrous tissue surrounding the cage. Each interface was then subclassified as to whether or not there was bone growth into the cage from the respective interface. Thus each disc interspace-cage-end plate junction could be classified as either: (1) cage completely surrounded by bone with bone ingrowth (B—B), (2) cage completely surrounded by bone with fibrous or no ingrowth (B-F/E), (3) cage surrounded by fibrous tissue with fibrous ingrowth (F-F), or (4) cage surrounded by fibrous tissue and empty (F-E).

The presence or absence of a successful arthrodesis was determined from the sagittal microradiographs. If both disc interspace-cage-end plate interfaces were completely surrounded by bone and there was bone consolidation throughout the interspace, then the level was deemed to have a solid arthrodesis. If both interfaces were surrounded by fibrous tissue and the cage was empty, then level was deemed to have a failed arthrodesis. If one interface was surrounded by bone and the other with fibrous tissue, or if both interfaces were surrounded by fibrous tissue and the cage filled with fibrous tissue, then the level was deemed to have an intermediate result.

The third sagittal slice was mounted in polymethylmethacrylate for fluorochrome analysis. Using the Isomet Plus saw, 200 to 360 $\mu$m thick slices were obtained. These slices were then ground to a thickness of 100 $\mu$m using a Maruto ML-512D Speed Lapping machine (Maruto Instruments, Tokyo, Japan). A sagittal microradiograph was obtained of the specimen at a thickness of 100 $\mu$m to correlate with the fluorochrome analysis. After obtaining this microradiograph the slice was ground down to a thickness of 40 $\mu$m and mounted on a slide for fluorochrome analysis. The presence or absence of each marker around and within the cage allowed us to determine the relative time frame of bone revascularization around.and within the cage.

RESULTS: All 21 goats successfully underwent surgery and survived without difficulty during the length of the experiment. No cervical spine wound infection occurred. There were no neurologic complications.

Radiographic Results: None of the cages in any of the groups displaced. In group I there were three cages with lucencies. In group II there were four cages with lucencies. In group II none of the 21 cages exhibited any lucencies.

Microradiograph Results: The results of grading each individual cage-endplate-interface junction are summarized in Table I. The BMP filled cages had a greater number of interfaces surrounded by bone and a greater amount with bone ingrowth than either of the other two groups.

The arthrodesis success rate was greatest for the BMP filled cages at 95% followed by the HA coated (62%) and standard devices (48%). This difference was statistically significant (p=0.002). The unsuccessful arthrodesis rate was 14% for both HA coated and standard groups, and zero for the BMP filled cages. The intermediate results were 38% for the standard cage, 14% for the hydroxyapatite cage, and 5% for the BMP filled cage.

Biomechanical Data: Mean biomechanical stiffness data in axial compression, torsion, flexion, extension, and lateral bending is summarized by group in Table II. There were no statistical differences by group in any of the loading modes tested. While there were no statistically significant differences in stiffness in any loading mode by arthrodesis result, there was a tendency for a cage with a successful arthrodesis to be stiffer than a failed arthrodesis in axial compression, torsion, flexion, and extension.

Fluorochrome Analysis: There were ten cages in group I that exhibited bone formation completely around the cage. Seven of these cages (70%) exhibited bone revascularization after the three week injection and three (30%) after the six week injection. In group II, thirteen cages exhibited bone formation completely around the cage. Either of these (62%) exhibited revascularization after the three week injection, three (23%) after the six week injection, and two (15%) after the nine week injection. In group III, twenty cages exhibited bone formation completely around the cage. Nineteen of these (95%) exhibited bone revascularization after the three week injection and one (5%) after the six week injection.

Twenty-two of the sixty-three cages in all three groups exhibited bone growth within the cage. In group I, one cage of six (17%) exhibited bone revascularization after the six week injection, and five cages (83%) after the nine week injection. In group II all five cages exhibited bone revascularization after the nine week injection. In group III, three of eleven ages (27%) exhibited bone revascularization after the three week injection, six (55%) after the six week injection, and two (18%) after the nine week injection. Thus, in general, the BMP filled cages exhibited earlier revascularization of bone both around and within the cages compared to the other two groups.

CONCLUSION: The use of an intervertebral fusion cage filled with BMP resulted in a much higher arthrodesis rate and accelerated bone revascularization compared to either autogenous bone filled devices, or autogenous interbody bone grafts with or without plate stabilization.

EXAMPLE 2

Design: Twelve mature female sheep underwent single level midlumbar interbody fusion. All surgical dissections were performed in an identical fashion. Following preparation of the anterior fusion sites the implants were inserted. Sheep were treated with a Threaded Interbody Fusion Device (TIBFD) containing rhBMP-2 carried on a type I fibrillar collagen (Helistat)(n=6) in a single cage, lateral orientation through a retroperitoneal approach. Previous limbs of the study (all n=6) included TIBFD with autogenous bone plugs, autogenous bone plugs alone, or sham (empty) fusion sites. The sheep were allowed to graze immediately post-operatively and no external immobilization was used. All animals were sacrificed six months following surgery. Fourteen additional cadaver sheep spines had been obtained to determine baseline intervertebral mechanical stiffness measures.

Materials: The interbody fusion cages developed and manufactured by Sofamor Danek, Inc., Memphis, Tenn. were made of Ti-6A1-4V alloy and designed as closed cylinders. The devices were 14 mm in diameter and contained a screw-in endcap to allow for placement of graft materials. The device porosity as described by the manufacturer was 35% overall hole to metal ratio with increased porosity in contact with the intervertebral bodies. The mechanical load to yield is reported to be 80.000 Newtons (maximum human physiologic loads–10.000 Newtons). Cyclic compressive loading from 800 to 9.680 Newtons at 15 Hz over 5.000.000 cycles resulted in no observable microscopic damage or deformation.

The dose of rhBMP-2 was 0.43 mg/ml. The protein in its buffered solution was drip applied to commercial grade type I collagen (Helistat). The composite was then inserted into the cage chamber following which the cage cap was applied. The device was then inserted into the prepared fusion site.

Surgical procedure: A 10 cm rostral to caudal left flank incision was made under sterile conditions. Following incision of the lateral fascia of the external abdominal musculature, the retroperitoneal plane was identified. Proceeding through this plane the intervertebral disc between the L4 and L5 veterbral bodies was cleaned of soft tissue. Segmental vessels were not ligated unless required for additional exposure. The descending aorta was retracted to expose the anterior longitudinal ligament and anterior annulus. A 2 mm guide wire was placed transversely through the intervertebral disc bisecting the disc in the sagittal plane. A cannulated trephine punch was then used over the wire to create a left lateral annulotomy.

A blunt tip "bullet" shaped dilator 7 mm in diameter was used over the same wire to expand the disc space and place the annulus under tension. A four-prong outer sleeve was placed over the distractor and impacted so as to purchase the adjacent vertebral bodies. Side prongs in the disc space aided in maintaining distraction. The dilator was then removed. A bone cutting reamer was placed through the outer sleeve and used to create a transverse hole through the disc space. At least 3 mm of endplate and subchondral bone of the adjacent vertebral bodies were removed during the process. At this point the device was prepared and implanted. Routine closure of external abdominal muscular fascia, subcutaneous tissue and skin was performed.

Mechanical Testing: All sheep that had undergone surgery were mechanically tested for fusion stiffness following sacrifice. In addition, cadaver spines from fourteen untreated sheep were also tested to establish baseline parameters for the L4–L5 motion segment. The L4–L5 intervertebral segments (fusion sites) were tested for stiffness to sagittal and coronal plane bending moments (flexion, extension, right bending, left bending) in all eighteen sheep. For baseline measures, fourteen untreated cadaver sheep spines were also tested for stiffness at the L4–L5 intersegment in the same planes of motion.

Following sacrifice, the spinal columns from L3 to L6 were explanted. Intersegmental ligamentous tissues were retained. The transverse processes were trimmed to facilitate polymethylmethacrylate (PMMA) potting of the L3 and L6 vertebrae. The PMMA pots did not include the L3–L4 or the L5–L6 discs.

Non-destructive mechanical tests were performed with an MTS 812 servohydraulic testing machine. The specimen was mounted in an apparatus such that it was oriented perpendicular to the axis of actuation. One end of the specimen was fixed while the other was free to move and placed directly above the actuator. Pure bending moments were applied using a system of cables and pulleys. Rotational variable differential transformers (RVDT) were attached to the vertebral body via bone screws to measure rotation in the L4–L5 motion segment and to the free end to measure its angle with respect to horizontal. load-displacement data were recorded.

For each test, loads were applied in three cycles consisting of a 5 second ramp per cycle with a maximum applied moment of approximately 10 N–m. Tests were performed in flexion, extension, right bending, and left bending modes sequentially. Stiffness was calculated as the slope of the force versus angular displacement curve at 8 N–m for all groups.

Radiographic Evaluation: Under general anesthesia, anterior-posterior and lateral radiographs were obtained immediately post-operatively, and then two months, four months, and six months following surgery. Measurements of vertebral body heights and disc heights along the lumbar spine were made in the mid-sagittal line using a photo image analyzer (superfine pitch monitor, Image-1/Atsoftware. 1991). All measurements were made on true lateral radiographs. Since measures of the interbody disc heights at the fusion sites were obscured by implant materials and "interbody height index" (IB index) was calculated to reflect interbody distraction. This index was calculated as follows: The mid-sagittal span of the fused segments from the cephalad endplate of L4 to the caudal endplate of L5 was measured as the "fusion height". Since the vertebrae were of relatively uniform height, the sum of the mid-sagittal heights of the L3 and L6 vertebrae was used to estimate the some of the heights of the L4 and L5 vertebrae excluding the intervening intervertebral disc. The sum of the L3 and L6 vertebrae was then subtracted from the fusion height to ascertain the "calculated interbody height". In order to correct for differences in magnification this value was expressed as a ratio to average vertebral height and this value was defined as the IB index.

Results: The mechanical testing results from one specimen implanted with TIBFD+rhBMP-2 were excluded due to apparatus errors.

Results of Mechanical Testing Data: Means, standard deviations as a function of group are presented in Table III. Results from overall and pairwise statistical comparisons are presented in Table IV. Mean stiffness was significantly different among the groups (two treatment and unoperated control) for each mode of testing (P=0.005, P=0.0001, P=0.0001, P=0.0001).

All surgically treated intersegments were significantly stiffer than untreated intersegments. That is, sites implanted with TIBFD+rhBMP-2 or TIBFD+autograft compared to those untreated were significantly stiffer to flexion (P=0.0001, P=0.055) extension (P=0.0001, P=0.0001) right bending P=0.0001, P=0.0001) and left bending moments (P=0.0001, P=0.0001). There was no difference in stiffness between intersegments treated with TIBFD+rhBMP-2 and those treated with TIBFD+autograft (comparisons for all modes of testing were P 0.05).

Results of Interbody Height Measures Interbody Height Index: Means standard deviations and results from overall and pairwise statistical comparisons are presented in Table V. There is no differences in the Interbody Height index between TIBFD+rhBMP-2 and TIBFD+autograft at each of the time measures F(4.40)=0.20 P=94). Subsidence occurred primarily in the first two post-operative months in both groups (roughly 20% of the initial interbody disc height) although the decrease in interbody height was not significant (F(2.20)=0.19, P=0.83).

Conclusions: No differences were noted either mechanically or morphologically between the fusions created with TIBFD+rhBMP-2 and those created with TIBFD+autograft. There was a trend toward greater stiffness to flexion with TIBFD+rhBMP-2 but this was not significant. Subsidence tended to occur in both groups in the first two months. Harvesting of autogenous bone graft provides no advantage compared to the use of rhBMP-2 with type I fibrillar collagen in this model.

EXAMPLE 3

Open Porosity Polylactic Acid Polymer (OPLA) is provided in sterile packaged 12.0 mm×6.5 mm×30 mm strips (two strips per package). The pure OPLA is sterilized via gamma irradiation. The rhBMP-2 is provided in freeze-dried powder form and reconstituted intra-operatively in sterile water and supplemented with a buffer vehicle solution. The rhBMP-2 is introduced into the carrier material and the carrier is placed into the hollow interior of a metal fusion cage device. The device is then implanted at the fusion site.

EXAMPLE 4

A rhBMP-2 /collagen implant is prepared from Helistat® Absorbably Collagen Hemostatic Agent (Integra Life-Sciences Corporation) and rhBMP-2. The collagen carrier is placed within the hollow interior of a metal fusion cage device. The device is implanted at the fusion site.

TABLE I

Individual Cage-Interspace-Endplate Bone Ingrowth Results by Cage Group

| Group | Microradiograph Grade* | | | |
|---|---|---|---|---|
| | B-B | B-F/E | F-F | F-E |
| I | 33% | 29% | 14% | 24% |
| II | 26% | 43% | 12% | 19% |
| III | 53% | 45% | 0% | 2% |

*See text for definition of each grading result.

TABLE II

Biomechanical Stiffness Data by Cage Group

| Group | Axial Compression (N/mm) | Torsion (N-m/degree) | Flexion (N-m/degree) | Extension (N-m/degree) | Lateral Bending (N-m/degree) |
|---|---|---|---|---|---|
| I | 187 (92) | 8.4 (11.7) | 0.99 (0.91) | 5.0 (7.2) | 1.4 (2.2) |
| II | 165 (70) | 10.2 (12.5) | 1.6 (2.7) | 3.4 (2.8) | 2.3 (3.9) |
| III | 313 (388) | 6.7 (10.2) | 0.96 (0.48) | 3.1 (2.4) | 1.0 (0.66) |
| p value | 0.46 | 0.32 | 0.24 | 0.82 | 0.72 |

Values in parenthesis represent standard deviations

TABLE III

Results of Mechanical Testing

| Conditions | n | Flexion Mean ± sd | Extension Mean ± sd | Rt. Bending Mean ± sd | Lt. Bending Mean ± sd |
|---|---|---|---|---|---|
| TIBFD + rhBMP-2 | 5* | 15.91 ± 6.90 | 25.19 ± 10.91 | 19.35 ± 5.82 | 15.40 ± 2.35 |
| TIBFD + autograft | 6 | 11.00 ± 7.81 | 24.55 ± 10.51 | 9.89 ± 4.04 | 19.47 ± 8.56 |
| Untreated | 14 | 6.71 ± 1.40 | 6.03 ± 2.15 | 0.41 ± 0.11 | 4.04 ± 0.90 |
| | 25 | | | | |

TABLE IV

Results of Mechanical Testing

| Compared Conditions | Flexion Mean ± sd. | P | Extension Mean ± sd. | P | Right Bending Mean ± sd. | P | Left Bending Mean ± sd. | P |
|---|---|---|---|---|---|---|---|---|
| TIBFD + rhBMP-2 | 15.91 ± 6.90 | (P = 0.30) | 25.19 ± 10.91 | (P = 0.92) | 19.35 ± 5.82 | (P = 0.36) | 15.40 ± 2.35 | (P = 0.33) |
| TIBFD + autograft | 11.00 ± 7.81 | | 24.55 ± 10.51 | | 15.58 ± 9.89 | | 19.47 ± 8.56 | |
| TIBFD + rhBMP-2 | 15.91 ± 6.90 | (P = 0.0001) | 25.19 ± 10.91 | (P < 0.0001) | 19.15 ± 5.82 | (P < 0.0001) | 15.40 ± 2.35 | (P < 0.0001) |
| Untreated | 6.71 ± 1.40 | | 6.03 ± 2.15 | | 2.98 ± 0.41 | | 4.04 ± 0.90 | |
| TIBFD + autograft | 11.00 ± 7.81 | (P = 0.06) | 24.55 ± 10.51 | (P < 0.0001) | 15.58 ± 9.89 | (P < 0.0001) | 19.47 ± 8.56 | (P < 0.0001) |
| Untreated | 6.71 ± 1.40 | | 6.03 ± 2.15 | | 2.98 ± 0.41 | | 4.04 ± 0.90 | |

TABLE V

Results Interbody Height Index: from 0 to 6 months

| Conditions | n | post op Mean ± sd | 2 months Mean ± sd | 4 months Mean ± sd | 6 months Mean ± sd |
|---|---|---|---|---|---|
| TIBFD + rhBMP-2 | 6* | 0.20 ± 0.04 | 0.14 ± 0.03 | 0.17 ± 0.04 | 0.15 ± 0.03 |
| TIBFD + autograft | 6 | 0.20 ± 0.03 | 0.15 ± 0.05 | 0.15 ± .05 | 0.16 ± .05 |
| Total measured | 12 | | | | |

EXAMPLE 5

Testing Rationale

Testing was conducted on endcaps to measure the resistance of the endcap to expulsion by a rhBMP-2 soaked collagen sponge and to compare the resistance to a known polyethylene endcap.

TEST A

Press-Fit Endcap Pushout Test

This test was conducted to determine the static force required to dislodge a polyethylene press-fit endcap from a BAK™ (Spine Tech, Minneapolis, Minn.) device. The endcap was snap-fit to the BAK™ device and an axial load was applied through the cavity of the BAK™ device to the endcap. The push-out load for five (5) samples ranged from 12 to 37 pounds of force.

TEST B

Test Set-Up and Methods

Five (5) samples of a titanium 12 mm endcap (894-120, Sofamor Danek, USA) (894-XXX, Sofamor Danek, USA, Memphis, Tenn.) were each placed into a 12 mm titanium NOVUS™LT (Sofamor Danek, USA) implant as shown in FIGS. 18 and 19. The 12 mm implant was fixed rigidly to the table of a closed loop servohydraulic test machine. The actuator of the testing machine was attached to the endcap via an adaptor which was threaded into the endcap. An axial load was applied to pull the endcap out at a rate of 25 mm/min until the endcap was completely removed from the 12 mm implant. The data, including maximum load and displacement, were recorded and plotted using Superscope II data acquisition software.

Results

All endcaps pulled out via elastic deflection of the two anchor prongs. The mean pull-out load was 187N (41.99 lbf). Table 1 shows the raw data for the pull-out tests.

TEST C

The methods of Test B were repeated on nine (9) samples except that the load was applied at a rate of 12.5 mm/min. The mean pull-out load was 30.57 Mean Force in Pounds. The 30.57 value compares well to the Test B value of 41.99 The sample size for this testing was 9, while the sample size of Test B was 5.

Discussion and Conclusions

The testing results show that the endcap of this invention is resistant to explusion in vivo for two reasons. First, it is well known that the intervertebral disc is under complex, combined loading. However, none of the loads acting on the disc space would act directly on the endcap of the implant in order to cause endcap explusion. Secondly, it is unlikely that the rhBMP-2 soaked collagen sponge could exert 177 N (41.99 lbf) of force to expulse the endcap.

The anchor prong endcaps of this invention were easily inserted into the devices by hand. In one instance, the endcap was inserted via the servohydraulic test machine. The insertion load was measured and found to be 3.2 lbf. This provides additional support for the solid endcap engagement. The average expulsion force is 13 times the insertion load.

The anchor prong endcaps of this invention compared very favorably to a known polyethylene press-fit endcap design. The press-fit cap averaged 25 pounds force with a range of 12 to 37 pounds. The anchor prong cap of this invention exceeded those values with a mean of 30.57 pounds and a range of 12.5 to 46.62 pounds of force over nine (9) samples.

While the invention has been described in detail in the foregoing description, the same is to be considered as illustrative and not restrictive in character, it being understood that only the preferred embodiments have been shown and described, and that all changes and modifications that come within the spirit of the invention are desired to be protected.

What is claimed:

1. A fusion device for facilitating arthrodesis in the disc space between adjacent vertebrae, comprising:
    a hollow load bearing body having an outer surface engageable with the adjacent vertebrae and an internal surface defining a chamber and an osteogenic material in said chamber to promote fusion between the adjacent vertebrae and a first opening in communication with said chamber, said body defining a second opening extending from said internal surface to said outer surface; and
    a cap having an occlusion body configured for engagement with said first opening to resist expulsion of said osteogenic material from said chamber and an elongate anchor projecting from said occlusion body, said anchor including a first end attached to said occlusion body and an opposite second end having engaging means for engaging said second opening to hold said occlusion body within said first opening, said means for engaging includes a lip defined on said second end, wherein said lip extends at least partially into said second opening.

2. The fusion device of claim 1, wherein said occlusion body further includes a tool engagement opening.

3. The fusion device of claim 2, wherein said tool engagement opening defines an internal thread.

4. The fusion device of claim 1, wherein said lip only partially occludes said second opening in said load bearing body.

5. A fusion device for facilitating arthrodesis in the disc space between adjacent vertebrae, comprising:
    a hollow load bearing body having an outer surface and an internal surface defining a chamber for an osteogenic material and a first opening in communication with said chamber, said body defining a second opening separated from said first opening with said load bearing body and extending from said internal surface to said outer surface; and
    a cap having an occlusion body configured for engagement with said first opening and an elongate anchor projecting from said occlusion body and extending along said load bearing body, said anchor including a first end attached to said occlusion body and an opposite second end having engaging means for engaging said second opening to hold said occlusion body within said first opening, wherein said occlusion body includes at least one aperture therethrough for fluid communication with said chamber.

6. A fusion device for facilitating arthrodesis in the disc space between adjacent vertebrae, comprising:
    a hollow load bearing body having an outer surface and an internal surface defining a chamber, an osteogenic material in said chamber, and a first opening in communication with said chamber, said body defining a second opening extending from said internal surface to said outer surface; and
    a cap having an occlusion body configured for engagement with said first opening and an elongate anchor projecting from said occlusion body, said anchor including a first end attached to said occlusion body and an opposite second end having engaging means for engaging said second opening to hold said occlusion body within said first opening, wherein said engaging means includes a leading edge having a first width and a trailing edge having a second larger width, wherein said trailing edge engages at least a portion of said second opening to retain said occlusion body in said first opening.

7. A fusion device for facilitating arthrodesis in the disc space between adjacent vertebrae, comprising:
    a hollow load bearing body having an outer surface and an internal surface defining a chamber for an osteogenic material and a first opening in communication with said chamber, wherein said hollow load bearing body has a length and said outer surface defines a pair of opposing cylindrical portions engageable with the adjacent vertebrae and a pair of substantially flat opposing side walls disposed between said cylindrical portions, said side walls extending along a substantial portion of said length, said body defining a second opening separated from said first opening with said load bearing body in one of said sidewalls and extending from said internal surface to said outer surface; and
    a cap having an occlusion body configured for engagement with said first opening and an elongate anchor projecting from said occlusion body, said anchor including a first end attached to said occlusion body and an opposite second end having engaging means for engaging said second opening to hold said occlusion body within said first opening.

8. The device of claim 7, wherein said second opening is formed in one of said flat opposing side walls.

9. A fusion device for facilitating arthrodesis in the disc space between adjacent vertebrae, comprising:
    a hollow load bearing body having an outer surface and an internal surface defining a chamber for an osteogenic material and a first opening in communication with said chamber, said body defining a second opening extending from said internal surface to said outer surface on one side of said body and a third opening extending from said internal surface to said outer surface on another side of said body, said second and third openings separated from said first opening with said load bearing body; and
    a cap having an occlusion body configured for engagement with said first opening and an elongate anchor extending from said occlusion body along said load bearing body, said anchor including a first end attached to said occlusion body and an opposite second end having engaging means for engaging said second opening and said third opening to hold said occlusion body within said first opening.

10. A fusion device for facilitating arthrodesis in the disc space between adjacent vertebrae comprising:
    a tubular body having a wall engageable with the adjacent vertebrae, said wall defining a chamber and bone growth material in said chamber for promoting fusion of the adjacent vertebrae, said body having a first end and an opposite second end, said first end defining an end opening, said wall defining a wall opening therethrough separated from said end opening with said wall; and a cap having an occlusion body configured to be at least partially received within said end opening to block expulsion of bone growth material from said chamber and an anchor projecting from said occlusion body extending along said wall of said tubular body, said anchor having a first end attached to said occlusion body and an opposite second end having an engagement projection, said engagement projection configured to engage said wall opening to secure said occlusion body within said end opening.

11. The device of claim 10, wherein said anchor is formed of a resilient material permitting deflection of said anchor during insertion into said tubular body.

12. The device of claim 10, wherein said occlusion body includes at least one osteogenic aperture formed therethrough.

13. The device of claim 10, wherein said occlusion body has a plurality of osteogenic openings formed therethrough.

14. The device of claim 10, wherein said occlusion body includes a flange, said flange configured to engage said first end to limit movement of said occlusion body into said end opening.

15. The device of claim 14, wherein said tubular body includes an internal shoulder adjacent said first end, said flange configured to engage said internal shoulder.

16. The device of claim 15, wherein said occlusion body includes an outer surface, wherein said outer surface is in substantial alignment with said first end when said flange engages said internal shoulder.

17. The device of claim 10, wherein said device includes at least two wall openings and said cap includes at least two anchors adapted to engage said at least two wall openings.

18. The device of claim 10, wherein said end opening has a first perimeter and said internal chamber has a second perimeter, said first perimeter and said second perimeter substantially equal, wherein said end opening provides substantially unobstructed access to said chamber.

19. The device of claim 9, wherein said engaging means includes a first anchor projection and a second anchor projection, said first anchor projection having a lip for engaging said second opening and said second anchor projection having a lip for engaging said third opening.

20. The device of claim 9, wherein said second opening and said third opening are opposite one another about said outer surface.

21. The device of claim 1, wherein said outer surface extends between opposite first and second ends of said hollow load bearing body and said second opening is positioned between said opposite first and second ends.

22. The device of claim 5, wherein said outer surface extends between opposite first and second ends of said hollow load bearing body and said second opening is positioned between said opposite first and second ends.

23. The device of claim 6, wherein said outer surface extends between opposite first and second ends of said hollow load bearing body and said second opening is positioned between said opposite first and second ends.

24. The device of claim 7, wherein said outer surface extends between opposite first and second ends of said hollow load bearing body and said second opening is positioned between said opposite first and second ends.

25. The device of claim 9, wherein said outer surface extends between opposite first and second ends of said hollow load bearing body and said second and third openings are positioned between said opposite first and second ends.

26. The device of claim 10, wherein said tubular body extends between opposite first and second ends and said second opening is positioned between said opposite first and second ends.

\* \* \* \* \*